(12) United States Patent
LaVon et al.

(10) Patent No.: US 7,618,404 B2
(45) Date of Patent: Nov. 17, 2009

(54) DISPOSABLE ABSORBENT ARTICLE HAVING DOUBLED SIDE FLAPS AND BACKSHEET STRIPS

(75) Inventors: Gary Dean LaVon, Liberty Township, OH (US); Kevin Michael Smith, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 429 days.

(21) Appl. No.: 11/159,916

(22) Filed: Jun. 23, 2005

(65) Prior Publication Data

US 2006/0293638 A1 Dec. 28, 2006

(51) Int. Cl.
*A61F 13/15* (2006.01)

(52) U.S. Cl. ............... 604/385.28; 604/385.29; 604/385.3; 604/385.24; 604/385.25

(58) Field of Classification Search ............ 604/385.28, 604/385.29, 385.3, 385.24, 385.25
See application file for complete search history.

(56) References Cited

U.S. PATENT DOCUMENTS

| | | |
|---|---|---|
| 1,733,997 A | 10/1929 | Marr |
| 1,734,499 A | 11/1929 | Marinsky |
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |

(Continued)

FOREIGN PATENT DOCUMENTS

DE 19732499 2/1999

(Continued)

OTHER PUBLICATIONS

U.S. Appl. No. 11/286,614, filed Nov. 23, 2005, LaVon.

(Continued)

*Primary Examiner*—Jacqueline F. Stephens
(74) *Attorney, Agent, or Firm*—Richard L. Alexander

(57) ABSTRACT

A disposable absorbent article includes two laterally opposing longitudinally extending backsheet strips attached to an exterior surface of an absorbent assembly in laterally opposing attachment zones. Each backsheet strip may include a water-impermeable layer and may be extensible. The absorbent assembly includes a lower covering sheet that is doubled by folding and thereby includes a first layer and a second layer. The absorbent assembly also includes laterally opposing side flaps which are formed by folding doubled portions of the lower covering sheet laterally inward. A longitudinally extending elastic gathering member is attached to each side flap adjacent to its proximal edge. When the article is worn, the elastic gathering members contract and raise the side flaps to form side barriers.

21 Claims, 14 Drawing Sheets

U.S. PATENT DOCUMENTS

| | | |
|---|---|---|
| 2,898,912 A | 8/1959 | Adams |
| 2,931,361 A | 4/1960 | Sostsrin |
| 2,977,957 A | 4/1961 | Clyne |
| 3,207,158 A | 9/1965 | Yoshitake et al. |
| 3,386,442 A | 6/1968 | Sabee |
| 3,561,446 A | 2/1971 | Jones |
| 3,572,342 A | 3/1971 | Lindquist et al. |
| 3,592,194 A | 3/1971 | Duncan |
| 3,578,155 A | 5/1971 | Small et al. |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 8/1974 | Zoephel |
| 3,840,418 A | 10/1974 | Sabee |
| 3,847,702 A | 11/1974 | Jones |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,074,508 A | 2/1978 | Reid |
| 4,084,592 A | 4/1978 | Tritsch |
| 4,100,922 A | 7/1978 | Hernandez |
| 4,257,418 A | 3/1981 | Hessner |
| 4,296,750 A | 10/1981 | Woon et al. |
| 4,315,508 A | 2/1982 | Bolick |
| 4,324,246 A | 4/1982 | Mullane et al. |
| 4,341,216 A | 7/1982 | Obenour |
| 4,342,314 A | 8/1982 | Radel et al. |
| 4,388,075 A | 6/1983 | Mesek et al. |
| 4,461,621 A | 7/1984 | Karami et al. |
| 4,463,045 A | 7/1984 | Ahr et al. |
| 4,475,912 A | 10/1984 | Coates |
| 4,490,148 A | 12/1984 | Beckeström |
| 4,527,990 A | 7/1985 | Sigl |
| 4,578,072 A | 3/1986 | Lancaster |
| 4,578,702 A | 3/1986 | Campbell |
| 4,585,450 A | 4/1986 | Rosch et al. |
| 4,589,878 A | 5/1986 | Mitrani |
| 4,601,717 A | 7/1986 | Blevins |
| 4,606,964 A | 8/1986 | Wideman |
| 4,610,678 A | 9/1986 | Weisman et al. |
| 4,623,342 A | 11/1986 | Ito et al. |
| 4,636,207 A | 1/1987 | Buell |
| 4,641,381 A | 2/1987 | Heran et al. |
| 4,670,011 A | 6/1987 | Mesek |
| 4,670,012 A | 6/1987 | Johnson |
| 4,680,030 A | 7/1987 | Coates et al. |
| 4,681,581 A | 7/1987 | Coates |
| 4,690,680 A | 9/1987 | Higgins |
| 4,695,278 A | 9/1987 | Lawson |
| 4,704,115 A | 11/1987 | Buell |
| 4,704,116 A | 11/1987 | Enloe |
| 4,731,066 A | 3/1988 | Korpman |
| 4,747,846 A | 5/1988 | Boland et al. |
| 4,781,711 A | 11/1988 | Houghton et al. |
| 4,787,896 A | 11/1988 | Houghton et al. |
| 4,795,454 A | 1/1989 | Dragoo |
| 4,802,884 A | 2/1989 | Fröidh et al. |
| 4,808,176 A | 2/1989 | Kielpikowski |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,846,825 A | 7/1989 | Enloe et al. |
| 4,861,652 A | 8/1989 | Lippert et al. |
| 4,888,231 A | 12/1989 | Angstadt |
| 4,892,528 A | 1/1990 | Suzuki et al. |
| 4,892,536 A | 1/1990 | DesMarais et al. |
| 4,900,317 A * | 2/1990 | Buell .................. 604/370 |
| 4,904,251 A | 2/1990 | Igaue et al. |
| 4,909,802 A | 3/1990 | Ahr et al. |
| 4,909,803 A | 3/1990 | Aziz et al. |
| 4,940,463 A | 7/1990 | Leathers et al. |
| 4,940,464 A | 7/1990 | Van Gompel et al. |
| 4,950,264 A | 8/1990 | Osborn |
| 4,963,140 A | 10/1990 | Robertson et al. |
| 4,968,313 A | 11/1990 | Sabee |
| 4,990,147 A | 2/1991 | Freeland |
| 5,006,394 A | 4/1991 | Baird |
| 5,019,072 A | 5/1991 | Polski |
| 5,021,051 A | 6/1991 | Hiuke |
| 5,032,120 A | 7/1991 | Freeland et al. |
| 5,034,008 A | 7/1991 | Breitkopf |
| 5,037,416 A | 8/1991 | Allen et al. |
| 5,071,414 A | 12/1991 | Elliott |
| 5,085,654 A | 2/1992 | Buell |
| 5,092,861 A | 3/1992 | Nomura et al. |
| 5,114,420 A | 5/1992 | Igaue et al. |
| 5,135,522 A | 8/1992 | Fahrenkrug et al. |
| D329,697 S | 9/1992 | Fahrenkrug et al. |
| 5,151,092 A | 9/1992 | Buell et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,246,431 A | 9/1993 | Minetola et al. |
| 5,246,432 A | 9/1993 | Suzuki et al. |
| 5,246,433 A | 9/1993 | Hasse et al. |
| 5,260,345 A | 11/1993 | Desmarais et al. |
| 5,269,775 A | 12/1993 | Freeland et al. |
| 5,292,316 A | 3/1994 | Suzuki |
| 5,312,386 A | 5/1994 | Correa et al. |
| 5,358,500 A | 10/1994 | LaVon et al. |
| 5,366,782 A | 11/1994 | Curro et al. |
| 5,387,209 A | 2/1995 | Yamamoto et al. |
| 5,397,316 A | 3/1995 | LaVon et al. |
| H1440 H | 5/1995 | New et al. |
| 5,476,458 A | 12/1995 | Glaug et al. |
| 5,507,895 A | 4/1996 | Suekane |
| 5,518,801 A | 5/1996 | Chappell et al. |
| 5,531,730 A | 7/1996 | Dreier |
| 5,542,943 A | 8/1996 | Sageser |
| 5,549,592 A | 8/1996 | Fries |
| 5,549,593 A | 8/1996 | Ygge et al. |
| 5,554,145 A | 9/1996 | Roe et al. |
| 5,569,234 A | 10/1996 | Buell et al. |
| 5,571,096 A | 11/1996 | Dobrin et al. |

| | | | | | | |
|---|---|---|---|---|---|---|
| 5,580,411 | A | 12/1996 | Nease et al. | 6,322,552 B1 | 11/2001 | Blenke et al. |
| 5,584,829 | A | 12/1996 | Lavash et al. | 6,325,787 B1 | 12/2001 | Roe et al. |
| 5,607,416 | A | 3/1997 | Yamamoto et al. | 6,334,858 B1 | 1/2002 | Rönnberg et al. |
| 5,607,537 | A | 3/1997 | Johnson et al. | 6,336,922 B1 | 1/2002 | VanGompel et al. |
| 5,607,760 | A | 3/1997 | Roe | 6,350,332 B1 | 2/2002 | Thomas et al. |
| 5,609,587 | A | 3/1997 | Roe | 6,364,863 B1 | 4/2002 | Yamamoto et al. |
| 5,613,959 | A | 3/1997 | Roessler et al. | 6,402,729 B1 | 6/2002 | Boberg et al. |
| 5,622,589 | A | 4/1997 | Johnson et al. | 6,402,731 B1 | 6/2002 | Suprise et al. |
| 5,624,424 | A | 4/1997 | Saisaka et al. | 6,413,249 B1 | 7/2002 | Turi et al. |
| 5,625,222 | A | 4/1997 | Yoneda et al. | 6,419,667 B1 | 7/2002 | Avalon et al. |
| 5,626,571 | A | 5/1997 | Young et al. | 6,423,048 B1 | 7/2002 | Suzuki et al. |
| 5,635,191 | A | 6/1997 | Roe et al. | 6,432,098 B1 | 8/2002 | Kline et al. |
| 5,643,243 | A | 7/1997 | Klemp | 6,432,099 B2 | 8/2002 | Rönnberg |
| 5,643,588 | A | 7/1997 | Roe et al. | 6,443,933 B1 | 9/2002 | Suzuki et al. |
| H1674 | H | 8/1997 | Ames et al. | 6,461,342 B2 | 10/2002 | Tanji et al. |
| 5,662,638 | A | 9/1997 | Johnson et al. | 6,461,343 B2 | 10/2002 | Schaefer et al. |
| 5,674,215 | A | 10/1997 | Ronnberg | 6,475,201 B2 | 11/2002 | Saito et al. |
| 5,685,874 | A | 11/1997 | Buell et al. | 6,478,786 B1 | 11/2002 | Glaug et al. |
| 5,691,035 | A | 11/1997 | Chappell et al. | 6,494,872 B1 | 12/2002 | Suzuki et al. |
| 5,695,488 | A | 12/1997 | Sosalla | 6,494,873 B2 | 12/2002 | Karlsson et al. |
| 5,723,087 | A | 3/1998 | Chappell et al. | 6,520,947 B1 | 2/2003 | Tilly et al. |
| 5,733,275 | A | 3/1998 | Davis et al. | 6,524,294 B1 | 2/2003 | Hilston et al. |
| 5,749,866 | A | 5/1998 | Roe et al. | 6,547,774 B2 | 4/2003 | Ono et al. |
| 5,752,947 | A | 5/1998 | Awolin | 6,570,056 B1 | 5/2003 | Tanzer et al. |
| 5,772,825 | A | 6/1998 | Schmitz | 6,572,601 B2 | 6/2003 | Suprise et al. |
| 5,776,121 | A | 7/1998 | Roe et al. | 6,572,602 B2 | 6/2003 | Furuya et al. |
| 5,779,831 | A | 7/1998 | Schmitz | 6,574,602 B1 | 6/2003 | Absar et al. |
| 5,797,894 | A | 8/1998 | Cadieux et al. | 6,579,275 B1 | 6/2003 | Pozniak et al. |
| 5,810,800 | A | 9/1998 | Hunter et al. | 6,585,712 B2 | 7/2003 | Yoshimasa |
| 5,814,035 | A | 9/1998 | Gryskiewicz et al. | 6,585,713 B2 | 7/2003 | LaMahieu et al. |
| 5,820,618 | A | 10/1998 | Roberts et al. | 6,602,234 B2 | 8/2003 | Klemp et al. |
| 5,846,232 | A | 12/1998 | Serbiak et al. | 6,605,070 B2 | 8/2003 | Ludwig et al. |
| 5,851,204 | A | 12/1998 | Mizutani | 6,626,881 B2 | 9/2003 | Shingu et al. |
| 5,858,013 | A | 1/1999 | Kling | 6,648,869 B1 | 11/2003 | Schlinz et al. |
| 5,865,823 | A | 2/1999 | Curro | 6,648,870 B2 | 11/2003 | Itoh et al. |
| 5,873,868 | A | 2/1999 | Nakahata | 6,648,871 B2 | 11/2003 | Kusibojoska et al. |
| 5,876,391 | A | 3/1999 | Roe et al. | 6,652,696 B2 | 11/2003 | Kuen et al. |
| 5,891,544 | A | 4/1999 | Chappell et al. | 6,682,515 B1 | 1/2004 | Mizutani et al. |
| 5,897,545 | A | 4/1999 | Kline et al. | 6,689,115 B1 | 2/2004 | Popp et al. |
| 5,904,673 | A | 5/1999 | Roe et al. | 6,706,028 B2 | 3/2004 | Roe et al. |
| 5,931,825 | A | 8/1999 | Kuen et al. | 6,716,205 B2 | 4/2004 | Popp et al. |
| 5,947,949 | A | 9/1999 | Inoue et al. | 6,726,792 B1 | 4/2004 | Johnson et al. |
| 5,951,536 | A | 9/1999 | Osborn, III et al. | 6,730,070 B2 | 5/2004 | Holmquist |
| 5,957,908 | A | 9/1999 | Kline et al. | 6,755,808 B2 | 6/2004 | Balogh et al. |
| 5,968,029 | A | 10/1999 | Chappell et al. | 6,818,083 B2 | 11/2004 | McAmish |
| 5,997,521 | A | 12/1999 | Robles et al. | 6,840,930 B1 | 1/2005 | Miyamoto et al. |
| 6,004,306 | A | 12/1999 | Robles et al. | 6,880,211 B2 | 4/2005 | Jackson et al. |
| 6,022,430 | A | 2/2000 | Blenke et al. | 6,923,797 B2 | 8/2005 | Shinohara et al. |
| 6,022,431 | A | 2/2000 | Blenke et al. | 7,318,820 B2 | 9/2005 | LaVon |
| 6,042,673 | A | 3/2000 | Johnson et al. | 6,962,578 B1 | 11/2005 | LaVon |
| 6,102,892 | A | 8/2000 | Putzer et al. | 6,972,010 B2 | 12/2005 | Pesce et al. |
| 6,107,537 | A | 8/2000 | Elder et al. | 7,013,941 B2 | 3/2006 | Schneider et al. |
| 6,110,157 | A | 8/2000 | Schmidt | 7,014,632 B2 | 3/2006 | Takino et al. |
| 6,117,121 | A | 9/2000 | Faulks et al. | 7,014,649 B2 | 3/2006 | Bacher |
| 6,117,803 | A | 9/2000 | Morman et al. | 7,037,299 B2 | 5/2006 | Turi et al. |
| 6,120,486 | A | 9/2000 | Toyoda et al. | 7,048,726 B2 | 5/2006 | Kusagawa et al. |
| 6,120,487 | A | 9/2000 | Ashton | 7,066,921 B2 | 6/2006 | Schmoker et al. |
| 6,120,489 | A | 9/2000 | Johnson et al. | 7,094,227 B2 | 8/2006 | Ishiguro et al. |
| 6,120,866 | A | 9/2000 | Arakawa et al. | 7,112,193 B2 | 9/2006 | Otsubo |
| 6,129,720 | A | 10/2000 | Blenke et al. | 7,195,622 B2 | 3/2007 | Lindstrom |
| 6,156,023 | A | 12/2000 | Yoshioka | 7,211,072 B2 | 5/2007 | Nawata et |
| 6,156,424 | A | 12/2000 | Taylor | 7,288,079 B2 | 10/2007 | Toyoshima et al |
| 6,165,160 | A | 12/2000 | Suzuki et al. | 7,291,137 B2 | 11/2007 | LaVon et al. |
| 6,174,302 | B1 | 1/2001 | Kumasaka | 7,314,465 B2 | 1/2008 | Van Gompel et al. |
| 6,177,607 | B1 | 1/2001 | Blaney | 7,320,684 B2 | 1/2008 | LaVon |
| 6,186,996 | B1 | 2/2001 | Martin | 7,347,848 B2 | 3/2008 | Fernfors |
| 6,210,386 | B1 | 4/2001 | Inoue | 7,377,914 B2 | 5/2008 | LaVon |
| 6,210,390 | B1 | 4/2001 | Karlsson | 7,435,244 B2 | 10/2008 | Schroer, Jr. et al. |
| 6,238,380 | B1 | 5/2001 | Sasaki | 2002/0045881 A1 | 4/2002 | Kusibojoska et al. |
| 6,241,716 | B1 | 6/2001 | Rönnberg | 2002/0087139 A1 | 7/2002 | Popp et al. |
| 6,254,294 | B1 | 7/2001 | Muhar | 2002/0151858 A1 | 10/2002 | Karami et al. |
| 6,306,122 | B1 | 10/2001 | Narawa et al. | 2002/0173767 A1 | 11/2002 | Popp et al. |
| 6,312,420 | B1 | 11/2001 | Sasaki et al. | 2003/0003269 A1 | 1/2003 | Lee et al. |

| | | | |
|---|---|---|---|
| 2003/0023220 A1 | 1/2003 | Ukegawa et al. | |
| 2003/0088223 A1 | 5/2003 | Vogt et al. | |
| 2003/0088230 A1 | 5/2003 | Balogh et al. | |
| 2003/0105447 A1 | 6/2003 | Widlund et al. | |
| 2003/0144644 A1 | 7/2003 | Murai et al. | |
| 2003/0148694 A1 | 8/2003 | Ghiam | |
| 2003/0233082 A1 | 12/2003 | Kline et al. | |
| 2004/0022998 A1 | 2/2004 | Miyamoto et al. | |
| 2004/0082928 A1 | 4/2004 | Pesce et al. | |
| 2004/0122404 A1 | 6/2004 | Meyer et al. | |
| 2004/0122411 A1 | 6/2004 | Hancock-Cooke | |
| 2004/0127868 A1 | 7/2004 | Olson et al. | |
| 2004/0147890 A1 | 7/2004 | Nakahata et al. | |
| 2004/0162536 A1 | 8/2004 | Becker et al. | |
| 2004/0167486 A1 | 8/2004 | Busam et al. | |
| 2004/0193133 A1 | 9/2004 | Desai et al. | |
| 2004/0225271 A1 | 11/2004 | Datta et al. | |
| 2004/0236299 A1 | 11/2004 | Tsang et al. | |
| 2004/0236304 A1 | 11/2004 | Coates et al. | |
| 2004/0249355 A1 | 12/2004 | Tanio et al. | |
| 2005/0004548 A1 | 1/2005 | Otsubo et al. | |
| 2005/0038401 A1 | 2/2005 | Suzuki et al. | |
| 2005/0085784 A1 | 4/2005 | LeMinh et al. | |
| 2005/0031373 A1 | 6/2005 | Wright | |
| 2005/0171499 A1 | 8/2005 | Nigam et al. | |
| 2005/0177126 A1 | 8/2005 | Kurata | |
| 2005/0203475 A1 | 9/2005 | LaVon et al. | |
| 2005/0288645 A1 | 12/2005 | LaVon | |
| 2005/0288646 A1 | 12/2005 | LaVon | |
| 2006/0264860 A1 | 11/2006 | Beck | |
| 2006/0264861 A1 | 11/2006 | LaVon | |
| 2006/0271010 A1 | 11/2006 | LaVon | |
| 2006/0281005 A1 | 11/2006 | LaVon | |
| 2006/0293637 A1 | 12/2006 | LaVon | |
| 2006/0293638 A1 | 12/2006 | LaVon | |
| 2007/0032770 A1 | 2/2007 | LaVon | |
| 2007/0049897 A1 | 3/2007 | LaVon | |
| 2007/0066951 A1 | 3/2007 | LaVon | |
| 2007/0066952 A1 | 3/2007 | LaVon | |
| 2007/0066953 A1 | 3/2007 | LaVon | |
| 2007/0066954 A1 | 3/2007 | LaVon | |
| 2007/0118088 A1 | 5/2007 | LaVon | |
| 2007/0118089 A1 | 5/2007 | LaVon | |
| 2007/0118091 A1 | 5/2007 | LaVon | |
| 2007/0144660 A1 | 6/2007 | O'Sickey et al. | |
| 2007/0173780 A1 | 7/2007 | LaVon | |
| 2007/0173782 A1 | 7/2007 | LaVon | |
| 2007/0275868 A1 | 11/2007 | Cooremans | |
| 2008/0183149 A1 | 7/2008 | LaVon | |
| 2008/0020815 A1 | 8/2008 | LaVon et al. | |
| 2008/0208155 A1 | 8/2008 | LaVon | |
| 2008/0208156 A1 | 8/2008 | LaVon | |
| 2008/0234649 A1 | 9/2008 | Hamall | |

FOREIGN PATENT DOCUMENTS

| | | | |
|---|---|---|---|
| EP | 0 206 208 A1 | 12/1986 | |
| EP | 206208 | 4/1990 | |
| EP | 374542 | 6/1990 | |
| EP | 0 403 832 B1 | 12/1990 | |
| EP | 0 761 194 A2 | 3/1997 | |
| EP | 0 893 115 A2 | 1/1999 | |
| EP | 0 916 327 B1 | 5/1999 | |
| EP | 0 951 890 | 10/1999 | |
| EP | 0 951 890 A2 | 10/1999 | |
| EP | 0 793 469 B9 | 6/2002 | |
| EP | 1 224 922 A2 | 7/2002 | |
| EP | 1 447 066 A1 | 8/2004 | |
| EP | 1 447 067 A1 | 8/2004 | |
| ES | 2 213 491 A1 | 8/2004 | |
| FR | 2 566 631 A1 | 1/1986 | |
| FR | 2 612 770 A1 | 9/1988 | |
| FR | 2 810 234 A1 | 12/2001 | |
| GB | 1 307 441 | 2/1973 | |
| GB | 1 513 055 | 6/1978 | |
| GB | 2 101 468 A | 1/1983 | |
| GB | 2 262 873 | 7/1993 | |
| GB | 2 262 873 A | 7/1993 | |
| JP | 04 122256 A | 4/1992 | |
| JP | 11318980 | 11/1999 | |
| WO | WO 1995/16746 | 6/1995 | |
| WO | WO 1995/19753 | 7/1995 | |
| WO | WO 95/29657 A1 | 11/1995 | |
| WO | WO 1997/25891 | 7/1997 | |
| WO | WO 98/16179 A1 | 4/1998 | |
| WO | WO 1998/16179 | 4/1998 | |
| WO | WO 99/13813 A1 | 3/1999 | |
| WO | WO 03/009794 A3 | 2/2003 | |
| WO | WO 2003/009794 | 2/2003 | |
| WO | WO 2004/103234 | 12/2004 | |
| WO | WO 2004/105664 | 12/2004 | |
| WO | WO 2005/016200 | 2/2005 | |
| WO | WO 2005/081937 | 9/2005 | |
| WO | WO 2005/087164 A1 | 9/2005 | |
| WO | WO 2006/123976 | 11/2006 | |
| WO | WO 2007/000315 A1 | 1/2007 | |
| WO | WO 2007/034348 | 3/2007 | |

OTHER PUBLICATIONS

International Search Report.
U.S. Appl. No. 10/770,043, filed Feb. 2, 2004, Office Action dated Feb. 18, 2009.
U.S. Appl. No. 10/770,043, filed Feb. 2, 2004, Office Action dated Jan. 11, 2008.
U.S. Appl. No. 10/770,043, filed Feb. 2, 2004, Office Action dated Jul. 17, 2007.
U.S. Appl. No. 10/770,043, filed Feb. 2, 2004, Office Action dated Mar. 9, 2007.
U.S. Appl. No. 10/770,043, filed Feb. 2, 2004, Office Action dated Sep. 13, 2006.
U.S. Appl. No. 10/770,043, filed Feb. 2, 2004, Office Action dated Mar. 23, 2006.
U.S. Appl. No. 10/799,947, filed Mar. 10, 2005, Notice of Allowance dated Oct. 2, 2007.
U.S. Appl. No. 10/799,947, filed Mar. 10, 2005, Office Action dated Jul. 20, 2007.
U.S. Appl. No. 10/799,947, filed Mar. 10, 2005, Office Action dated Apr. 11, 2007.
U.S. Appl. No. 10/799,947, filed Mar. 10, 2005, Office Action dated Oct. 16, 2006.
U.S. Appl. No. 10/799,947, filed Mar. 10, 2005, Office Action dated Jul. 13, 2006.
U.S. Appl. No. 10/799,947, filed Mar. 10, 2005, Office Action dated Mar. 16, 2006.
U.S. Appl. No. 10/799,947, filed Mar. 10, 2005, Office Action dated Oct. 4, 2005.
U.S. Appl. No. 10/880,135, filed Nov. 8, 2005, Notice of Allowance dated Jun. 17, 2005.
U.S. Appl. No. 10/880,135, filed Nov. 8, 2005, Office Action dated Nov. 12, 2004.
U.S. Appl. No. 11/172,191, filed Jun. 29, 2004, Notice of Allowance dated Aug. 7, 2007.
U.S. Appl. No. 11/172,191, filed Jun. 29, 2004, Office Action dated Feb. 16, 2007.
U.S. Appl. No. 11/172,191, filed Jun. 29, 2004, Office Action dated Aug. 10, 2006.
U.S. Appl. No. 11/133,818, filed May 20, 2005, Office Action dated Apr. 1, 2009.
U.S. Appl. No. 11/133,818, filed May 20, 2005, Office Action dated Dec. 9, 2008.
U.S. Appl. No. 11/133,818, filed May 20, 2005, Office Action dated Jun. 18, 2008.
U.S. Appl. No. 11/133,818, filed May 20, 2005, Office Action dated Dec. 31, 2007.

U.S. Appl. No. 11/133,818, filed May 20, 2005, Office Action dated Jun. 26, 2007.
U.S. Appl. No. 11/135,689, filed May 25, 2005, Office Action dated Feb. 24, 2009.
U.S. Appl. No. 11/135,689, filed May 25, 2005, Office Action dated Oct. 16, 2008.
U.S. Appl. No. 11/135,689, filed May 25, 2005, Office Action dated Apr. 3, 2008.
U.S. Appl. No. 11/135,689, filed May 25, 2005, Office Action dated Oct. 9, 2007.
U.S. Appl. No. 11/135,689, filed May 25, 2005. Office Action dated Jun. 4, 2007.
U.S. Appl. No. 11/135,689, filed May 25, 2005, Office Action dated Oct. 6, 2006.
U.S. Appl. No. 11/140,888, filed May 31, 2005, Office Action dated Dec. 30, 2008.
U.S. Appl. No. 11/140,888, filed May 31, 2005, Office Action dated Oct. 10, 2008.
U.S. Appl. No. 11/140,888, filed May 31, 2005, Office Action dated Mar. 28, 2008.
U.S. Appl. No. 11/140,888, filed May 31, 2005, Office Action dated Dec. 13, 2007.
U.S. Appl. No. 11/140,888, filed May 31, 2005, Office Action dated Jun. 27, 2007.
U.S. Appl. No. 11/158,563, filed Jun. 25, 2005, Office Action dated Dec. 24, 2008.
U.S. Appl. No. 11/158,563, filed Jun. 25, 2005, Office Action dated Sep. 5, 2008.
U.S. Appl. No. 11/158,563, filed Jun. 25, 2005, Office Action dated Oct. 5, 2007.
U.S. Appl. No. 11/197,197, filed Aug. 4, 2005, Office Action dated May 7, 2008.
U.S. Appl. No. 11/197,197, filed Aug. 4, 2005, Office Action dated Nov. 7, 2007.
U.S. Appl. No. 11/197,197, filed Aug. 4, 2005, Office Action dated Jul. 6, 2007.
U.S. Appl. No. 11/197,197, filed Aug. 4, 2005, Office Action dated Apr. 12, 2007.
U.S. Appl. No. 11/197,197, filed Aug. 4, 2005, Office Action dated Sep. 27, 2006.
U.S. Appl. No. 11/210,345, filed Aug. 24, 2005, Office Action dated Jan. 9, 2009.
U.S. Appl. No. 11/210,345, filed Aug. 24, 2005, Office Action dated Sep. 10, 2008.
U.S. Appl. No. 11/210,345, filed Aug. 24, 2005, Office Action dated Apr. 8, 2008.
U.S. Appl. No. 11/210,345, filed Aug. 24, 2005, Office Action dated Oct. 18, 2007.
U.S. Appl. No. 11/210,345, filed Aug. 24, 2005, Office Action dated Feb. 12, 2007.
U.S. Appl. No. 11/224,462, filed Sep. 12, 2005, Office Action dated May 5, 2009.
U.S. Appl. No. 11/224,462, filed Sep. 12, 2005, Office Action dated Dec. 12, 2008.
U.S. Appl. No. 11/224,462, filed Sep. 12, 2005, Office Action dated May 28, 2008.
U.S. Appl. No. 11/224,462, filed Sep. 12, 2005, Office Action dated Nov. 29, 2007.
U.S. Appl. No. 11/224,462, filed Sep. 12, 2005, Office Action dated Jul. 10, 2007.
U.S. Appl. No. 11/231,512, filed Sep. 21, 2005, Office Action dated Jan. 6, 2009.
U.S. Appl. No. 11/231,512, filed Sep. 21, 2005, Office Action dated Jun. 27, 2008.
U.S. Appl. No. 11/231,500, filed Sep. 21, 2005, Office Action dated Jan. 8, 2009.
U.S. Appl. No. 11/231,500, filed Sep. 21, 2005, Office Action dated Sep. 22, 2008.
U.S. Appl. No. 11/231,500, filed Sep. 21, 2005, Office Action dated Mar. 4, 2008.
U.S. Appl. No. 11/231,500, filed Sep. 21, 2005, Office Action dated Aug. 22, 2007.
U.S. Appl. No. 11/231,500, filed Sep. 21, 2005, Office Action dated Jun. 8, 2006.
U.S. Appl. No. 11/232,193, filed Sep. 21, 2005, Notice of Allowance dated Aug. 28, 2007.
U.S. Appl. No. 11/232,193, filed Sep. 21, 2005, Office Action dated Jun. 7, 2006.
U.S. Appl. No. 11/286,934, filed Nov. 23, 2005, Office Action dated May 30, 2008.
U.S. Appl. No. 11/286,934, filed Nov. 23, 2005, Office Action dated Dec. 31, 2007.
U.S. Appl. No. 11/286,934, filed Nov. 23, 2005, Office Action dated Jun. 28, 2007.
U.S. Appl. No. 11/286,614, filed Nov. 23, 2005, Office Action dated Jan. 2, 2009.
U.S. Appl. No. 11/286,614, filed Nov. 23, 2005, Office Action dated Jun. 11, 2008.
U.S. Appl. No. 11/709,500, filed Feb. 27, 2007, Office Action dated Sep. 25, 2008.
U.S. Appl. No. 11/713,906, filed Feb. 28, 2007, Office Action dated Apr. 13, 2009.
U.S. Appl. No. 11/713,906, filed Feb. 28, 2007, Office Action dated Jun. 26, 2008.

* cited by examiner

DISPOSABLE ABSORBENT ARTICLE HAVING DOUBLED SIDE FLAPS AND BACKSHEET STRIPS

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact.

As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

A disposable absorbent article includes two laterally opposing longitudinally extending backsheet strips attached to an exterior surface of an absorbent assembly in laterally opposing attachment zones. Each backsheet strip may include a water-impermeable layer and may be extensible. The absorbent assembly includes a lower covering sheet that is doubled by folding and thereby includes a first layer and a second layer. The absorbent assembly also includes laterally opposing side flaps which are formed by folding doubled portions of the lower covering sheet laterally inward. A longitudinally extending elastic gathering member is attached to each side flap adjacent to its proximal edge. When the article is worn, the elastic gathering members contract and raise the side flaps to form side barriers.

BRIEF DESCRIPTION OF THE DRAWINGS

In the accompanying drawing figures, like reference numerals identify structurally corresponding elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In the drawing figures and in the written description, lowercase letters appended to reference numerals indicate generally symmetric elements, e.g., the left and right side edges of the absorbent assembly 200 are respectively identified by the reference numerals 237a and 237b. A reference numeral without an appended lowercase letter identifies all of the elements to which that particular reference numeral applies, e.g., the same side edges as a group are designated 237.

In FIG. 1, the interior portion of the diaper 20 is shown facing the viewer.

DETAILED DESCRIPTION OF THE INVENTION

Figure 1:
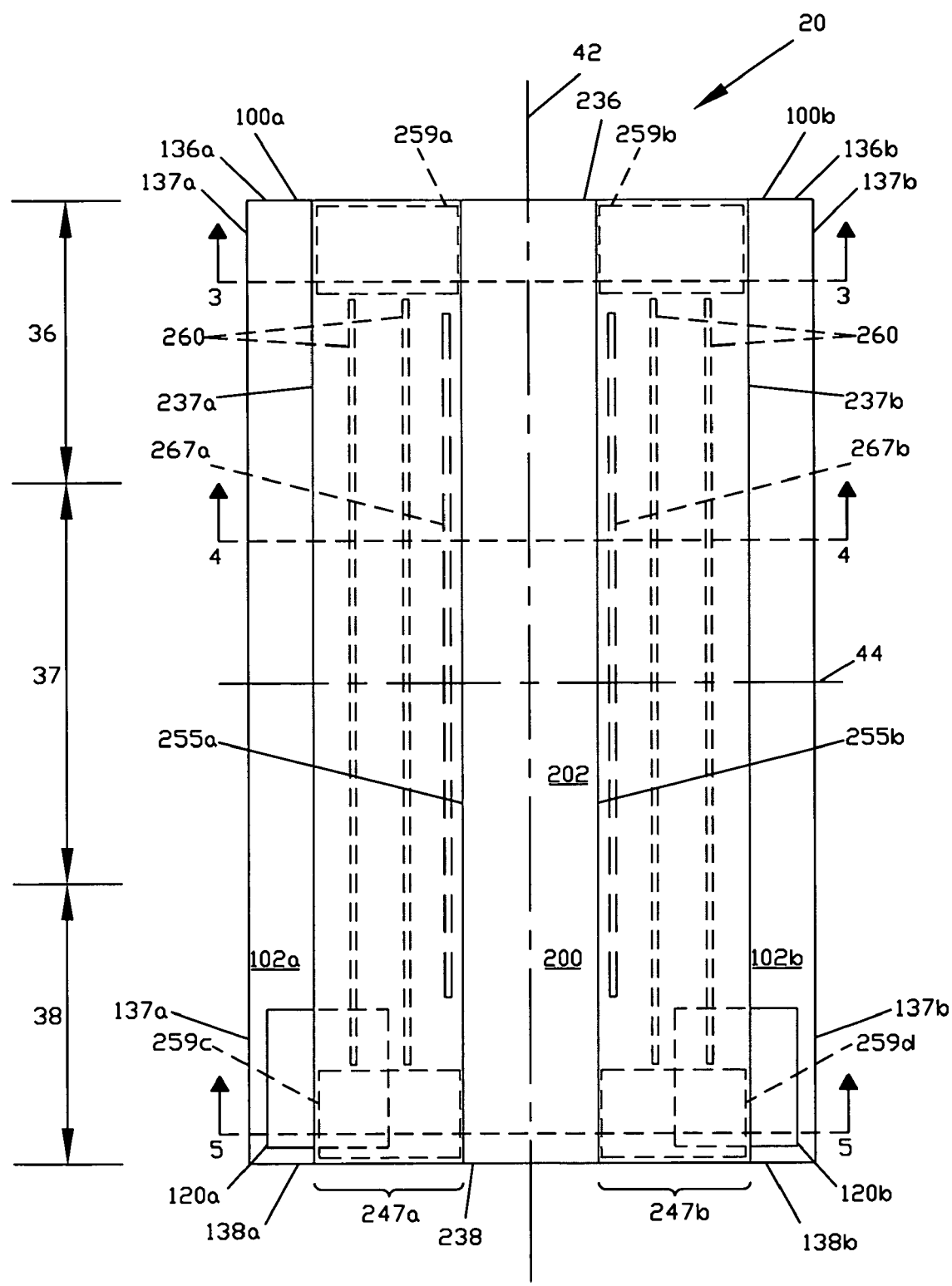
FIG. 1 is a plan view of an exemplary disposable diaper 20, which is shown in its flat, uncontracted state, i.e., without the contraction induced by elastic members.

In this description, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "diaper" refers to an absorbent article that is generally worn by infants and incontinent persons about the lower torso so as to encircle the waist and the legs of the wearer and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner.

The term "longitudinal" refers to a direction running from a waist edge to an opposing waist edge of the article and generally parallel to the maximum linear dimension of the article. Directions within 45° of the longitudinal direction are considered to be "longitudinal".

The term "lateral" refers to a direction running from a side edge to an opposing side edge of the article and generally at a right angle to the longitudinal direction. Directions within 45° of the lateral direction are considered to be "lateral".

The term "disposed" refers to an element being attached and positioned in a particular place or position in a unitary structure with other elements.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "cohesive" refers to the property of a material that, once set, sticks to itself but does not to any significant degree stick to other materials.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "proximal" and "distal" refer respectively to the location of an element relatively near to or far from the center of a structure, e.g., the proximal edge of a longitudinally extending element is located nearer to the longitudinal axis than the distal edge of the same element is located relative to the same longitudinal axis.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower", "above" and "below", "over" and "under", and "top" and "bottom", respectively.

Description of Exemplary Diaper Embodiments

Reference is made to FIG. 1, FIG. 2, FIG. 3, FIG. 4, FIG. 5, FIG. 6, FIG. 7, and FIG. 8 for this section of this description.

One end portion of the exemplary diaper 20 is configured as a front waist region 36, the longitudinally opposing end portion is configured as a back waist region 38, and an intermediate portion is configured as a crotch region 37.

The basic structure of the diaper 20 includes an absorbent assembly 200, which has a front edge 236, a back edge 238, laterally opposing side edges 237, an interior surface 202, and an exterior surface 204. A longitudinal axis 42 extends through the midpoints of the front edge 236 and the back edge 238 and a lateral axis 44 extends through the midpoints of the side edges 237. The absorbent assembly 200 has laterally opposing side flaps 247 and a lower covering sheet 25 that are described in more detail below.

The basic structure of the diaper 20 also includes two laterally opposing longitudinally extending backsheet strips designated the left backsheet strip 100a and the right backsheet strip 100b. The backsheet strips have respective front waist edges 136, back waist edges 138, proximal edges 156, interior surfaces 102, and exterior surfaces 104. Together, the two backsheet strips define the respective side edges 137 of the diaper 20.

The backsheet strips 100 and the lower covering sheet 25 are attached together in laterally opposing longitudinally extending attachment zones such as the exemplary attachment zones 220.

When the diaper 20 is worn on the lower torso of a wearer, the front waist edges 136 of the backsheet strips, the front edge 236 of the absorbent assembly, the back waist edges 138 of the backsheet strips, and the back edge 238 of the absorbent assembly encircle the waist of the wearer, the side edges 137 encircle the legs of the wearer, the crotch region 37 is generally positioned between the legs of the wearer, and the absorbent assembly 200 extends from the front waist region 36 through the crotch region 37 to the back waist region 38.

A portion or the whole of each of the backsheet strips may be formed of an elastically extensible material or materials. Alternatively, or in addition, a portion or the whole of each of the backsheet strips may be made extensible to a degree greater than the inherent extensibility of the material or materials from which the backsheet strip is made. Similarly, a portion of the absorbent assembly may be formed of an elastically extensible material or materials. Alternatively or in addition, a portion of the absorbent assembly may be made extensible to a degree greater than the inherent extensibility of the material or materials from which the absorbent assembly is made. The additional extensibility may be desirable in order to allow the diaper 20 to conform to the body of a wearer during movement by the wearer. Additional lateral extensibility may be particularly desirable to allow the user of a diaper to extend the front waist region and/or the back waist region to encircle the waist of a wearer, i.e., to tailor the waist size and fit of a diaper to the individual wearer. Such a lateral extension of the waist region or regions may give the diaper a generally hourglass shape and may impart a tailored appearance to the diaper when it is worn. In addition, the additional extensibility may be desirable in order to minimize the cost of the diaper, because a relatively lesser amount of material is needed when the material is made extensible as described.

For the purpose of fitting to the waist of the wearer, in some embodiments additional lateral extensibility in the absorbent assembly 200 is provided only between the laterally opposing attachment zones 220 where the absorbent assembly 200 and the backsheet strips 100 are attached together, rather than in the entire absorbent assembly.

Figure 9:
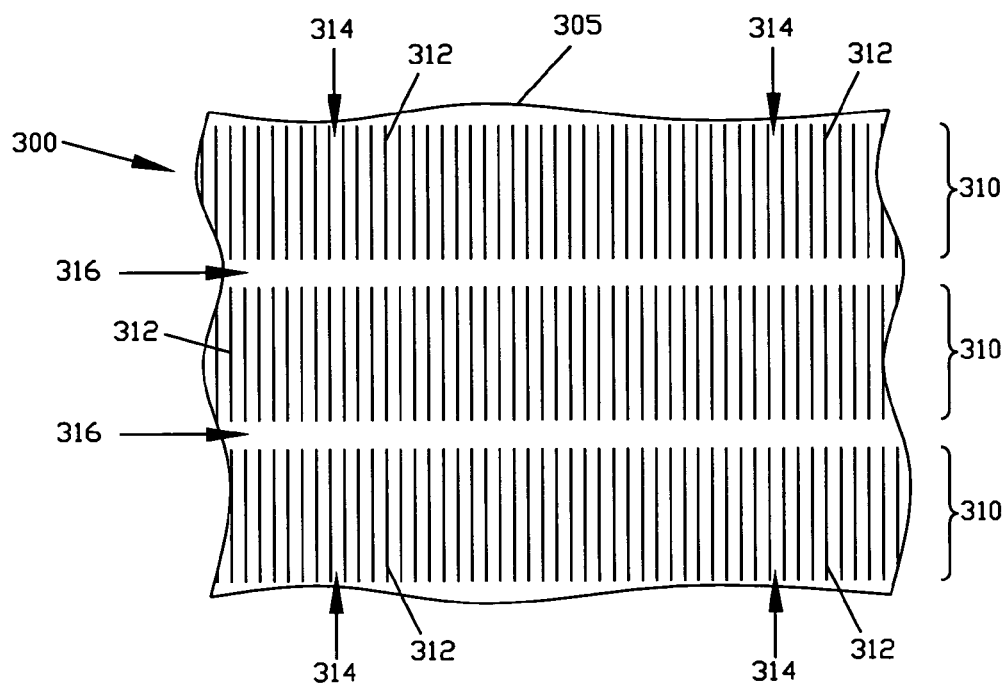
FIG. 9 is a plan view of an exemplary fragment of a formed web material.

Additional extensibility in the backsheet strips and/or the absorbent assembly may be provided in a variety of ways. For example, a material or materials from which the backsheet strips and/or the absorbent assembly is/are made may be pleated by any of many known methods. Alternatively, all or a portion of the backsheet strips and/or the absorbent assembly may be made of a formed web material or a formed laminate of web materials like those described in U.S. Pat. No. 5,518,801 issued on 21 May 1996 in the name of Chappell et al. An exemplary fragment 300 of such a formed web material 305 is shown in FIG. 9. This formed web material 305 includes distinct laterally extending regions 310 in which the original material has been altered by embossing or another method of deformation to create a pattern of generally longitudinally oriented alternating ridges 312 and valleys 314. The formed web material 305 also includes laterally extending unaltered regions 316 located between the laterally extending altered regions 310.

Such a formed web material 305 can be laterally extended beyond its original dimension with the application of relatively less force than that required to extend the same material to the same extent when undeformed. In particular, the application of opposing divergent forces directed generally perpendicular to the ridges 312 and valleys 314 extends such a formed web material along an axis between the opposing forces and generates a resistive contractive force, primarily in the unaltered regions 316. This resistive force is relatively smaller than the resistive force that is generated by the same material in its unaltered form when extended to the same extent, at least up to an extension at which the ridges and valleys in the altered regions flatten and begin to contribute to the resistive force. Thus, such formed web materials exhibit an extensible behavior resembling that of traditional elastic materials in the range of extensibility that is useful in absorbent articles, but may be made of relatively less expensive materials that are not inherently elastic and, thus, their use may provide an advantage in terms of the cost of manufacturing the absorbent articles.

In addition, different portions of the backsheet strips and/or the absorbent assembly may be formed to have different ranges of extensibility and/or to be extensible to a greater or lesser degree when subjected to a given level of opposing tensile forces, i.e., to be relatively more easily or less easily extensible. Such differential extensibility may be desirable so that, for example, one or both of the waist regions may be laterally extended relatively farther or relatively more easily than the crotch region.

Description of the Backsheet Strips

The diaper 20 includes two laterally opposing longitudinally extending backsheet strips designated the left backsheet strip 100a and the right backsheet strip 100b as shown in FIG. 1, FIG. 2, FIG. 3, FIG. 4, and FIG. 5. The backsheet strips may be formed of a nonwoven material, for example a synthetic nonwoven such as spunbonded or carded polyethylene, polypropylene, polyester, or rayon. Alternatively or in addition, each backsheet strip may include a water-impermeable layer that is formed of a suitable material, for example a film of polyethylene or another polyolefin, a microporous breathable film, a hydrophobic nonwoven, or a film formed of coextruded polyolefin layers. For example, a suitable coextruded film is available from Clopay Plastic Products Co. of Mason, Ohio, U.S.A. under the designation of M18-327. A multi-layer backsheet strip, such as a laminate of a film and a nonwoven, may also be suitable and may be oriented with the nonwoven disposed exteriorly to provide the feel and appearance of a cloth-like outermost layer, with the nonwoven disposed interiorly to separate the film from the skin of the wearer, or with nonwovens disposed both exteriorly and interiorly.

The front waist region and the back waist region can be fastened together in many ways to form a waist opening and two leg openings suitable for encircling the waist and the legs of the wearer. For example, separate fastening devices such as safety pins, separate tapes, a separate tie strap or straps, and/or a separate belt can be used for this purpose. Alternatively or in addition, fastening elements can be incorporated into the disposable absorbent article to enable a user to apply the diaper to the body of the wearer without, or in conjunction with, any separate fastening devices. Many suitable types of such incorporated fastening elements are well-known, including, for example, tapes, adhesives, adhesive tape tabs, ties, buttons, hooks, loops, snap fasteners, other forms of mechanical fasteners, cohesive patches, etc. Some suitable mechanical fasteners may be adapted to engage with a nonwoven, e.g., a nonwoven layer of a laminate backsheet or the lower covering sheet.

The fastening of the front waist region and the back waist region together may be openable and refastenable to allow for the adjustment of the fit of the diaper on the wearer and for the inspection of the interior of the diaper without fully removing it from the wearer. Alternatively, the fastening may be permanent, i.e., its opening may require the destruction of a portion of the diaper, e.g., the tearing of a portion of the diaper or the breaking of fused side seams.

Cohesive fastening patches may be formed by the application of a cohesive material onto a substrate. The cohesive material may be applied in any of a variety of patterns, such as a continuous film, discrete dots, stripes, polygons, etc., and/or spaced and interconnected geometric elements describing a grid. Suitable synthetic cohesive products are available from Andover Coated Products, Incorporated, of Salisbury, Mass., U.S.A. and are described in U.S. Pat. No. 6,156,424 issued on 5 Dec. 2000 in the name of Taylor.

Figure 10:
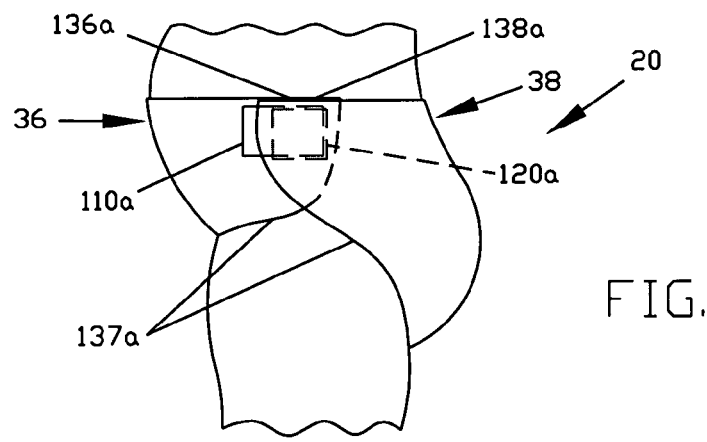
FIG. 10 and FIG. 11 are simplified left and right side elevation views of an exemplary diaper 20 including cohesive fastening patches being worn about a lower torso of a wearer.
Figure 11:
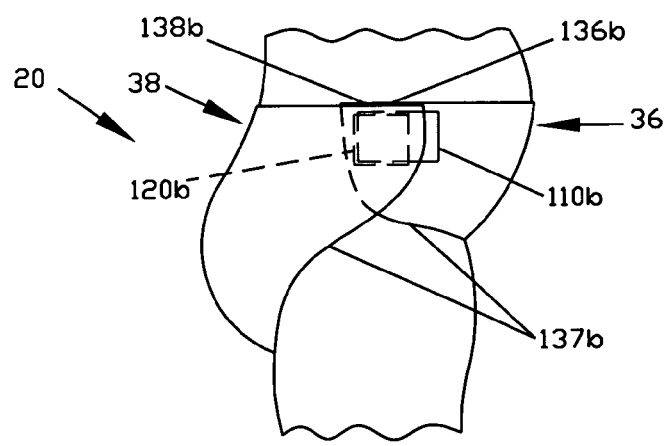

In FIG. 1, FIG. 2, FIG. 3, FIG. 5, FIG. 10, and FIG. 11, cohesive fastening patches 110a and 110b are shown disposed on the exterior surfaces of the respective backsheet strips 100a and 100b in the front waist region 36. In this exemplary embodiment, functionally complementary cohesive fastening patches 120a and 120b are disposed on the interior surfaces of the respective backsheet strips 100a and 100b in the back waist region 38. When the diaper 20 is worn as shown in FIG. 10 and FIG. 11, the cohesive fastening patches on the interior overlap the cohesive fastening patches on the exterior and the cohesion of the overlapped cohesive fastening patches fastens the front waist region 36 and the back waist region 38 together at the sides of the diaper 20. The configuration shown in these figures is adapted for back-over-front fastening.

Alternatively, the front cohesive fastening patches may be disposed on the interior of the diaper 20 and the back cohesive fastening patches may be disposed on the exterior of the diaper 20 in order to adapt the configuration for front-over-back fastening. Alternatively, the cohesive fastening patches may be disposed in a reversible configuration that is adapted to provide the user of the diaper with both options for fastening, i.e., either back-over-front or front-over-back, according to personal preference. For example, cohesive fastening patches that are disposed on both the exterior and the interior of the diaper 20 may allow a back cohesive fastening patch to overlap a front cohesive fastening patch or the front cohesive fastening patch to overlap the back cohesive fastening patch.

When the underlying portion of the diaper is extensible, it is preferable that the cohesive fastening patches be similarly extensible such that the underlying extensible portion of the diaper is not restrained.

Figure 12:
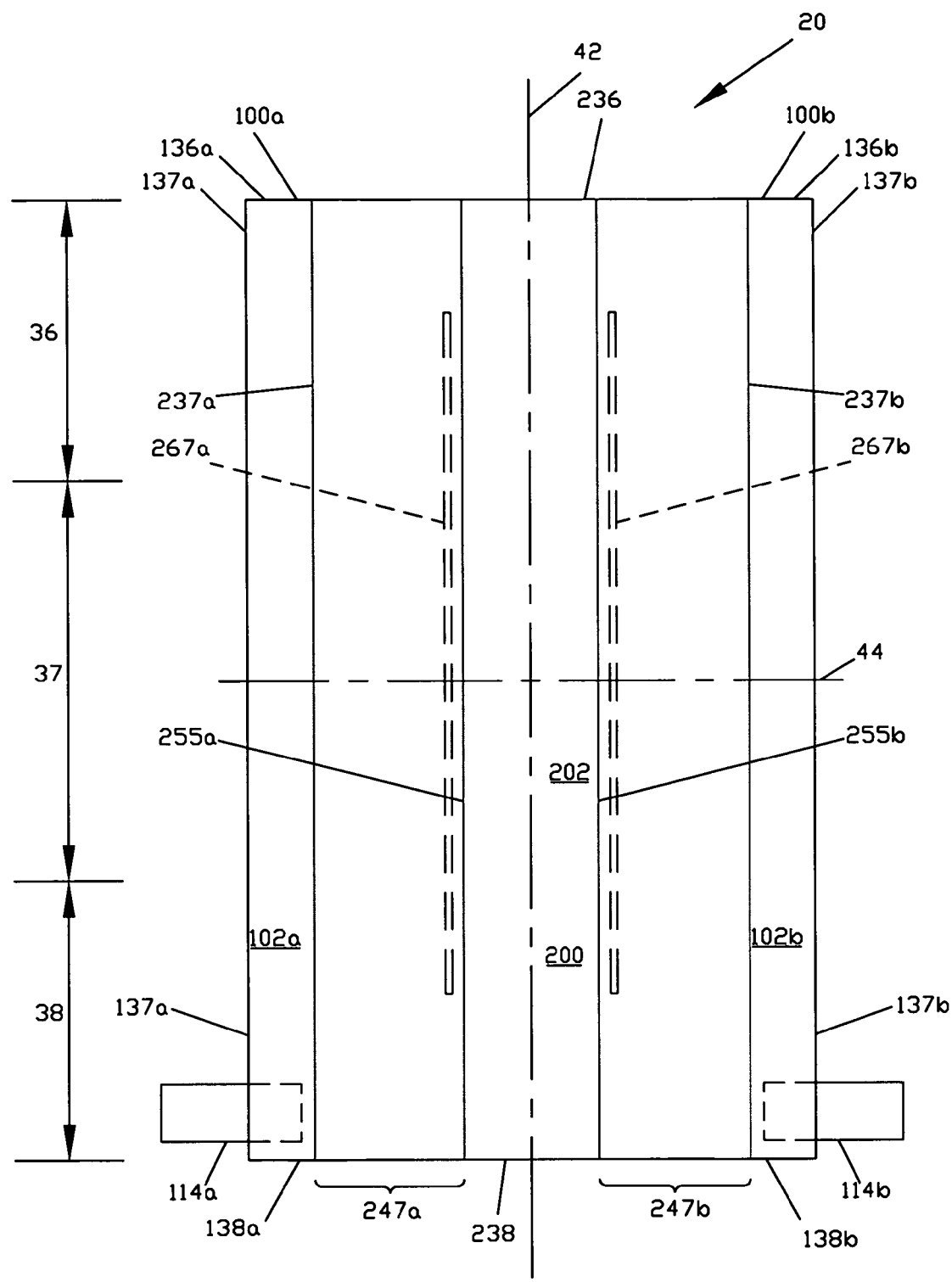
FIG. 12 is a simplified plan view of another exemplary disposable diaper 20, which is shown in its flat, uncontracted state and with its interior portion facing the viewer.
Figure 13:
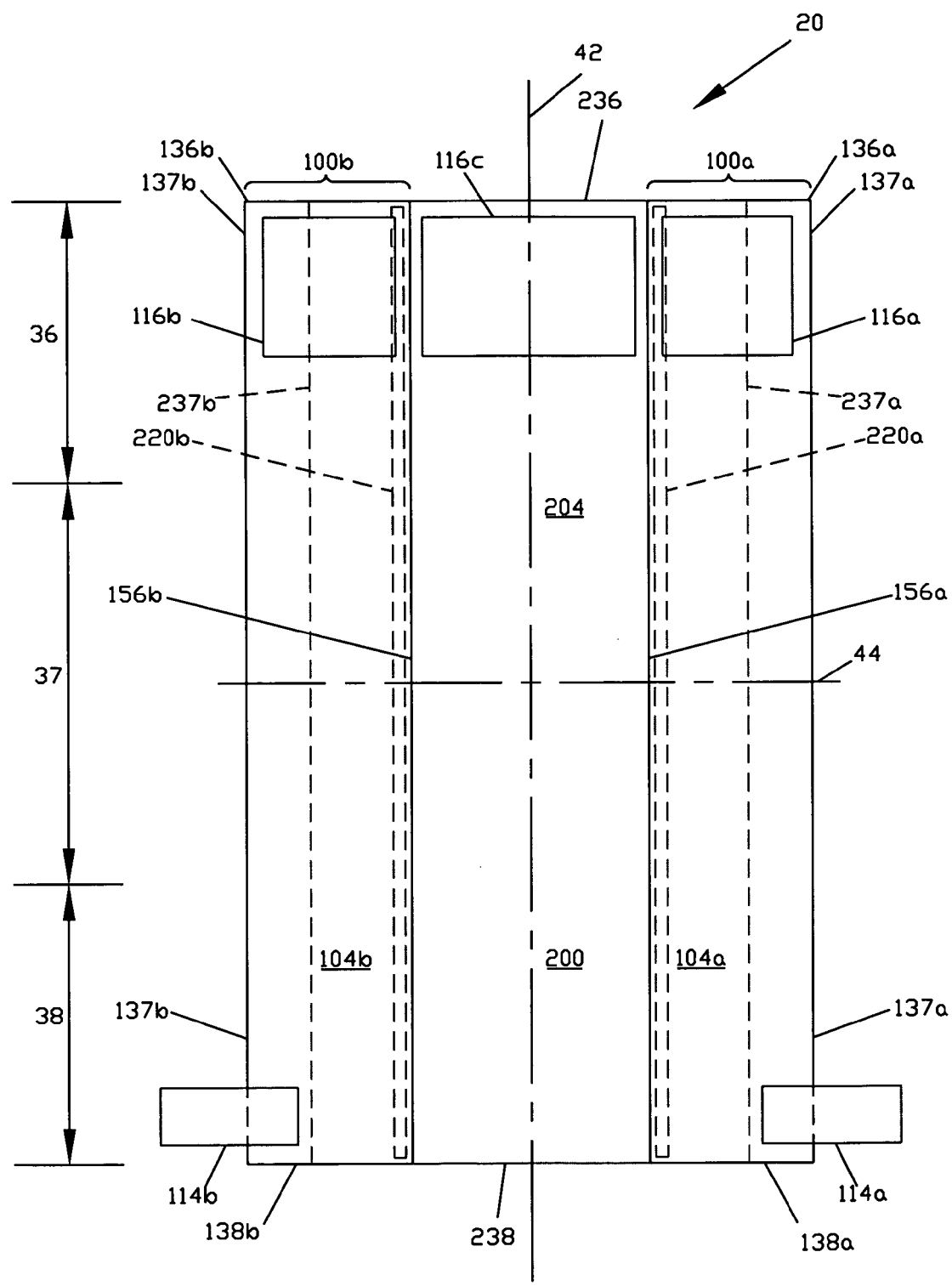
FIG. 13 is a simplified exterior plan view of the diaper 20 of FIG. 12.

Alternatively, adhesive tape tabs may be attached to the diaper 20 and may be used to fasten the back waist region 38 and the front waist region 36 together. For example, as shown in FIG. 12 and FIG. 13, laterally opposing adhesive tape tabs 114a and 114b may be attached to the respective backsheet strips 100a and 100b at or adjacent to the side edges 137a and 137b of the diaper 20. Suitable adhesive tapes are available from the 3M Corporation of St. Paul, Minn., U.S.A., under the designation of XMF99121, and from the Avery Dennison Corporation, Specialty Tape Division, Mentor, Ohio, U.S.A., under the designation of F4416.

Optionally, fastening sheets may also be attached to the diaper 20 and used in conjunction with such adhesive tape tabs. For example, fastening sheets 116 may be attached onto the exterior surfaces 104 of the respective backsheet strips 100 and/or the absorbent assembly 200 as shown in FIG. 13. When a fastening sheet is provided, the adhesive tape tabs may be adhered to the fastening sheet to fasten the back waist region 38 and the front waist region 36 together. The fastening sheet serves to distribute the tensile force transmitted by each of the adhesive tape tabs over an area larger than the adhered area of the adhesive tape tab and may, itself, bear a portion of the tensile force and thereby relieve a portion of the force exerted on the underlying portion of the diaper, such as the backsheet strips. Thus, for example, the incorporation of such a fastening sheet may make it possible to use a relatively inexpensive and relatively weak material for the underlying portion of the diaper. When mechanical fasteners are used instead of adhesive tape tabs, a fastening sheet can have a surface and/or elements that engage with the mechanical fastener, e.g., loops with which hooks may engage. When the underlying portion of the diaper is extensible, it is preferable that the fastening sheet be similarly extensible such that the underlying extensible portion of the diaper is not restrained.

Description of the Absorbent Assembly

As shown in FIG. 1, FIG. 2, FIG. 3, FIG. 4, and FIG. 5, the absorbent assembly 200 has laterally opposing side flaps 247 formed by folding portions of the absorbent assembly toward the longitudinal axis 42, to form both the respective side flaps 247 and the side edges 237 of the absorbent assembly 200. The absorbent assembly 200 may simply be folded loosely or may be creased along a portion of each of its side edges 237. For example, it may be desirable to form creases along portions of the side edges 237 in the crotch region 37 in order to impart a more finished appearance to the diaper 20. Alternatively or in addition to creasing, a portion of each of the folded side flaps 247 adjacent to the side edges 237 may be attached to the interior surface 202 of the absorbent assembly 200 to achieve a similar result. The side flaps may overlap the absorbent core 250, i.e., the proximal edges 255 of the side flaps may lie laterally inward of the respective side edges 257 of the absorbent core 250. Alternatively, the side flaps may not overlap the absorbent core.

In the exemplary diaper 20 shown in FIG. 1, the absorbent assembly 200 extends the full length of the backsheet strips 100 between the front waist edges 136 and the back waist edges 138. Such a full length configuration may be desirable in order to minimize the amount of waste material and the difficulty associated with the manufacture of the diaper 20, especially when the method used to manufacture the diaper 20 requires the introduction of the material or materials for the absorbent assembly 200 in the form of a continuous web or multiple continuous webs. Also, such a full length configuration may be desirable in order to isolate the skin of the wearer from the backsheet strips. Alternatively, the absorbent assembly 200 may be shorter and extend less than the full length of the backsheet strips. Such a shorter configuration may be desirable in order to minimize the total amount of material used and the cost of the diaper 20. As another alternative, the absorbent assembly 200 may extend longitudinally beyond the backsheet strips. Such a longer configuration may be desirable in order to minimize the total amount of material used in the backsheet strips and therefore the cost of the diaper 20.

Each of the side flaps 247 is attached to the interior surface 202 of the absorbent assembly 200 in attachment zones located at or adjacent to the front edge 236 and the back edge 238. For example, in the diaper 20 shown in FIG. 2, the left side flap 247a is attached to the interior surface 202 of the absorbent assembly 200 in attachment zones 251a and 251c, while the right side flap 247b is attached to the interior surface 202 in attachment zones 251b and 251d. The attachment zones may have equal areas or may be unequal in area.

Between the attachment zones, the proximal edges 255 of the side flaps 247 remain free, i.e., are not attached to the interior surface 202 of the absorbent assembly 200. Also between the attachment zones, each side flap preferably includes a longitudinally extensible flap elastic member that is attached adjacent to the proximal edge of the side flap. For example, in the diaper 20 shown in FIG. 1, elastic strands 267 are attached adjacent to the respective proximal edge 255 of the side flaps. The flap elastic member may be sandwiched between two layers of the absorbent assembly or may be attached on a surface of the absorbent assembly and remain exposed.

Figure 14:
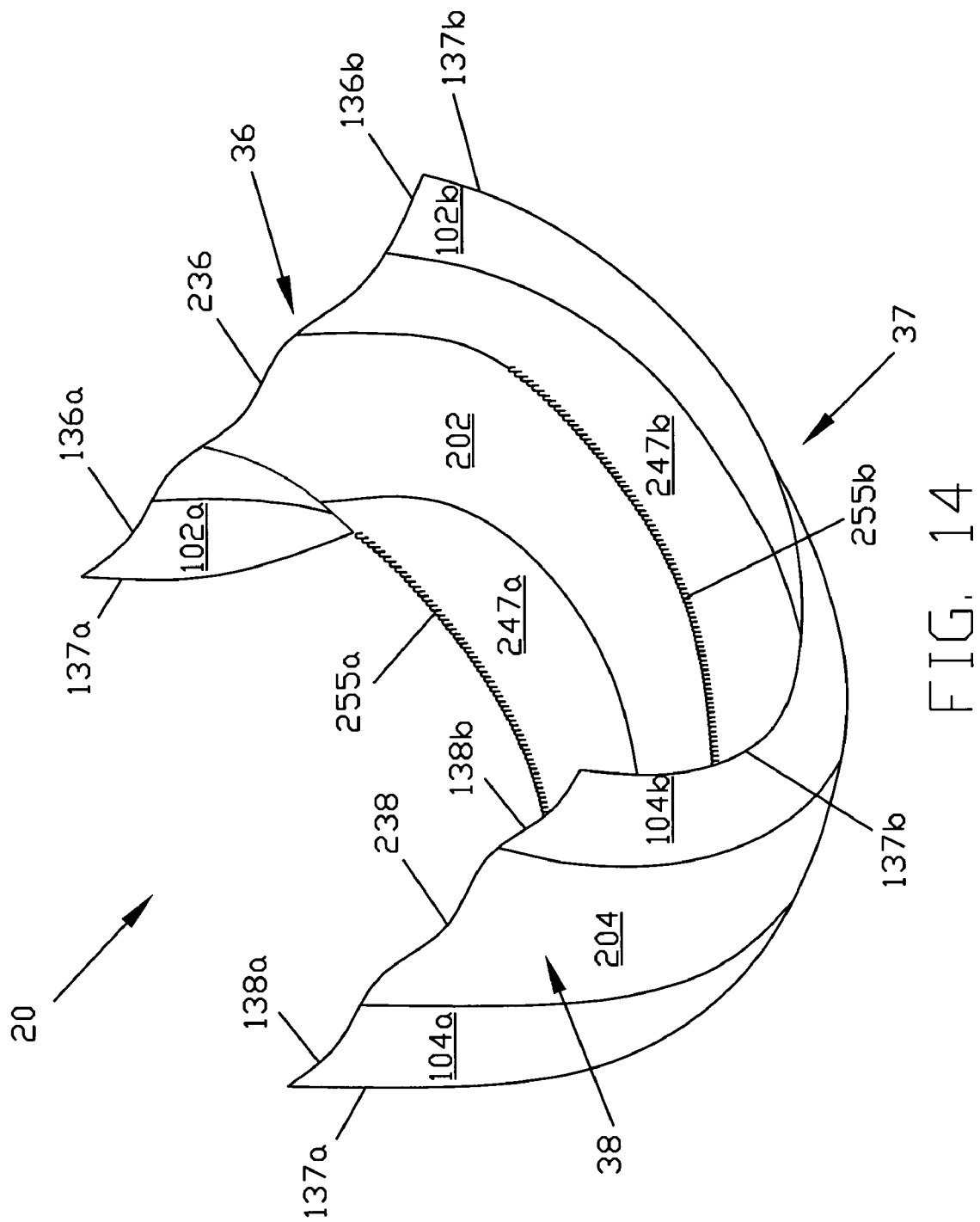
FIG. 14 is a perspective view of an exemplary diaper 20, which is shown in its relaxed, contracted state and with its interior portion facing upward.

When stretched, the flap elastic members allow the proximal edges of the side flaps to extend to the flat uncontracted length of the absorbent assembly, as shown in FIG. 1. When allowed to relax, the flap elastic members contract to gather the portions of the proximal edges along which the flap elastic members are attached. For example, when the exemplary diaper 20 is in a relaxed condition as shown in FIG. 14, the elastic strands 267 contract to gather the proximal edges 255 of the side flaps 247. The contractive forces of the elastic strands pull the front waist region 36 and the back waist region 38 toward each other and thereby bend the absorbent assembly 200 and the entire diaper 20 into a "U" shape in which the interior of the "U" shape is formed by the interior portions of the diaper. Because the proximal edges remain free between the attachment zones, the contractive forces of the elastic strands lift the proximal edges 255 of the side flaps 247 away from the interior surface 202 of the absorbent assembly and thereby raise the side flaps into position to serve as side barriers. The lateral spacing of the lifted proximal edges is selected to allow the deposit of bodily wastes from the lower torso of the wearer into the space between the raised side flaps. The width of each of the side flaps 247 in effect becomes its height when the free portion of its proximal edge is lifted and the side flap is raised. This height preferably is selected to allow the lifted proximal edges 255 to fit into the leg creases of the body of the wearer to form seals to help prevent the leakage of deposited bodily waste out of the diaper.

Figure 15:
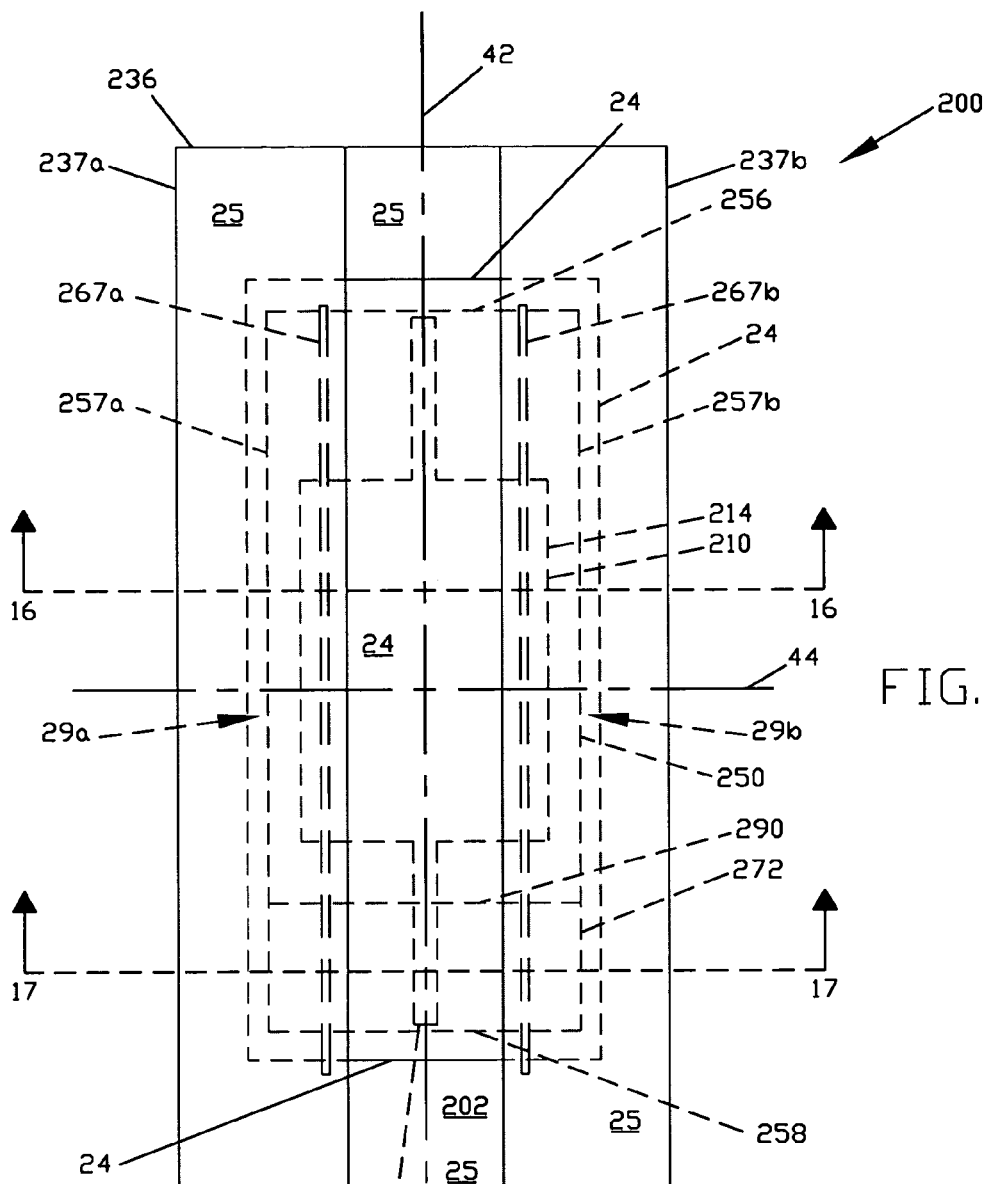
FIG. 15 is a plan view of an exemplary absorbent assembly 200, shown separately from the other portions of an exemplary diaper and with its interior portion facing the viewer.
Figure 16:
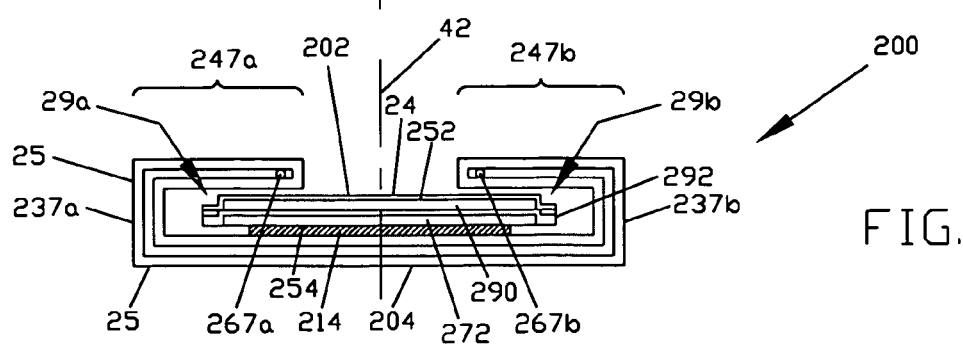
FIG. 16 is a view of the absorbent assembly of FIG. 15 taken at the section line 16-16.
Figure 17:
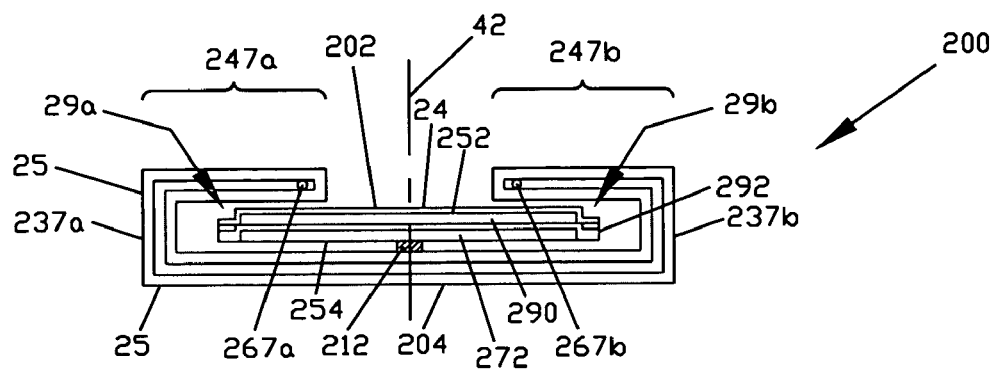
FIG. 17 is a view of the absorbent assembly of FIG. 15 taken at the section line 17-17.

As shown in FIG. 15, FIG. 16, and FIG. 17, the absorbent assembly 200 includes an absorbent core 250 that serves to absorb and retain liquid bodily waste materials. The absorbent core 250 has a front edge 256, a back edge 258, laterally opposing side edges 257, an interior surface 252, and an exterior surface 254.

The absorbent assembly 200 may include an upper covering sheet disposed above the absorbent core 250 in addition to a lower covering sheet is disposed below the absorbent core 250. If both are present, such an upper covering sheet and lower covering sheet may be attached together to contain the absorbent core 250 between them and thereby form the absorbent assembly 200. For example, in the exemplary absorbent assembly 200 shown in FIG. 15, FIG. 16, and FIG. 17, an upper covering sheet 24 and a lower covering sheet 25 are attached together in the laterally opposing attachment zones 29.

An upper covering sheet, if present, is water-permeable and allows liquid bodily waste to pass through its thickness to the absorbent core. The upper covering sheet preferably is formed of a soft material that will not irritate the skin of the wearer, for example a synthetic nonwoven such as spunbonded or carded polyethylene, polypropylene, polyester, or rayon.

The lower covering sheet 25 is doubled by folding and thereby includes a first layer 27 and a second layer 28 at least in the side flaps 247, i.e., at least between each side edge 237 and the respective proximal edge 255 of the side flap 247, both layers 27 and 28 are present, while between the side edges 237 below the absorbent core 250, only one of the layers 27 and 28 needs to be present. In some exemplary embodiments, both the first layer 27 and the second layer 28 are present over substantially the entire area of the lower covering sheet 25. In both of these variations of the structure, the side flap elastic members 267 are sandwiched between the first layer 27 and the second layer 28 adjacent to the proximal edges 255 of the side flaps 247. Doubling by folding is a particularly easy and cost-effective way of processing sheet materials in a manufacturing system, in part because it obviates the need to precisely align the edges of separate sheets when forming a doubled structure. In addition, doubling by folding makes it unnecessary to attach the doubled layers together, at least at the fold, although the layers can be attached together wherever desired for certain purposes, as explained below.

The proximal edge 255 of at least one of the side flaps 247 is formed where the lower covering sheet 25 is folded for doubling. For example, in the exemplary embodiment shown in FIG. 1, FIG. 2, FIG. 3, FIG. 4, and FIG. 5, both of the proximal edges 255 of the side flaps 247 are formed by the folding of the lower covering sheet 25 for doubling. In this embodiment, the lower covering sheet 25 is folded twice to form the two proximal edges 255 and the layers 27 and 28 are overlapped and attached together adjacent to the original longitudinally extending edges 33 of the lower covering sheet 25 in the longitudinally extending attachment zone 35 disposed below the absorbent core 250. Alternatively, the attachment zone 35 may be disposed laterally differently from the location shown in these figures. For example, the attachment zone 35 may be disposed adjacent to one of the side edges 237 of the absorbent assembly 200 or may be disposed between one of the proximal edges 255 of one of the side flaps 247 and the respective side edge 237. As another example, the lower covering sheet 25 may be folded only once at the proximal edge 255 of one of the side flaps 247 and the attachment zone 35 where the layers 27 and 28 are attached together may be disposed adjacent to the proximal edge 255 of the laterally opposing side flap 247 such that the original longitudinally extending edges 33 are exposed there. As an alternative to overlapping the original longitudinally extending edges 33, the original edges 33 may be laterally spaced and the lower covering sheet 25 may be attached in two laterally spaced attachment zones 35 adjacent to the two original edges 33 to one other structural element, such as the absorbent core 250, or to two other structural elements, such as the backsheet strips 100.

The layers 27 and 28 of the doubled lower covering sheet 25 may remain unattached to each other and thus free to contact each other or separate from each other. Alternatively, the layers of the doubled lower covering sheet 25 may be attached together laterally continuously or intermittently between the proximal edges 255 of the side flaps 247 and the side edges 237 of the absorbent assembly 200. Alternatively, or in addition, the layers of the doubled lower covering sheet 25 may be attached together laterally continuously or intermittently below the absorbent core 250 between the side edges 237 of the absorbent assembly 200. For example, the layers of the doubled lower covering sheet 25 may be attached together by adhesives, mechanical bonds, or thermal bonds, or by a combination of known bonding methods.

Figure 2:
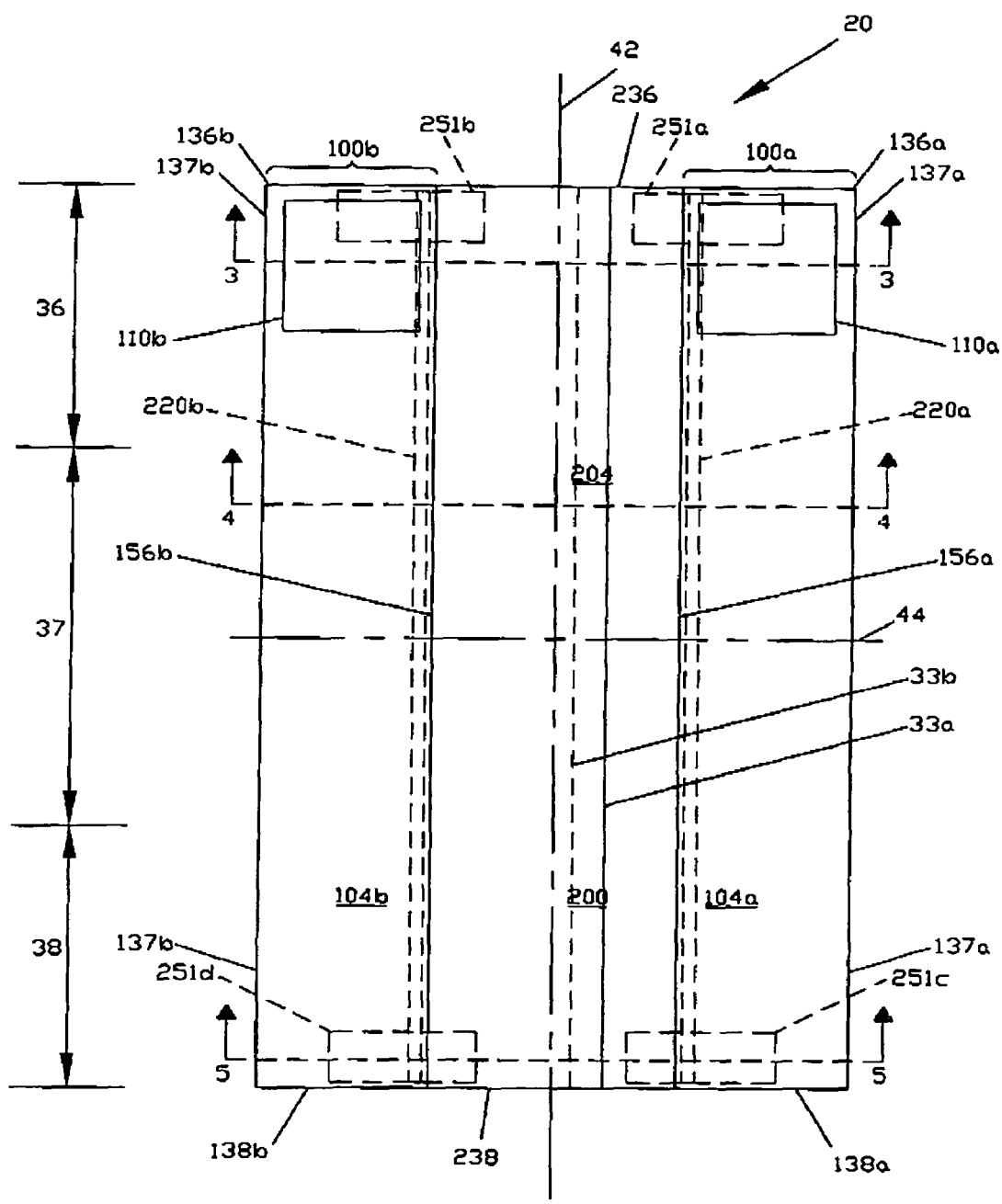
FIG. 2 is an exterior plan view of the diaper 20 of FIG. 1.
Figure 4:
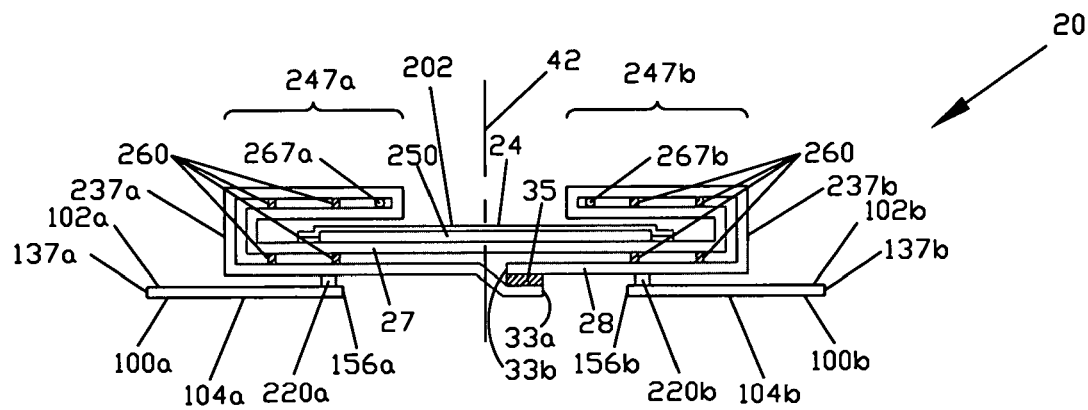

In the exemplary embodiment shown in FIG. 1, FIG. 2, and FIG. 4, the layers 27 and 28 are attached together in laterally spaced attachment zones 260 extending longitudinally through the crotch region 37 and into the waist regions 36 and 38. Such longitudinally extending attachment together prevents the layers from separating and thereby presenting an undesirable baggy or blousy appearance around the legs of the wearer, as well as tending to stiffen the side flaps 247 slightly and thereby helping to ensure their proper fit against the body.

Figure 3:
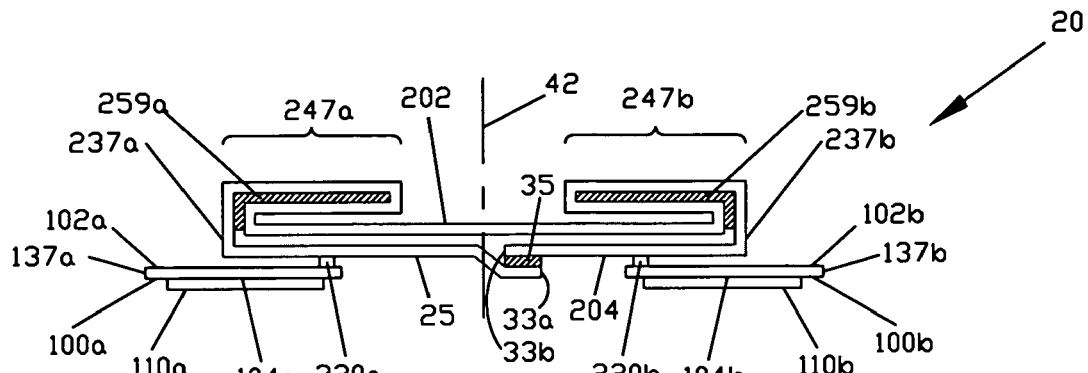
FIG. 3, FIG. 4, and FIG. 5 are section views of the diaper 20 of FIG. 1 and FIG. 2 taken at the respective section lines 3-3, 4-4, and 5-5. In these section views, the interior portion of the diaper 20 is shown facing upward.
Figure 5:
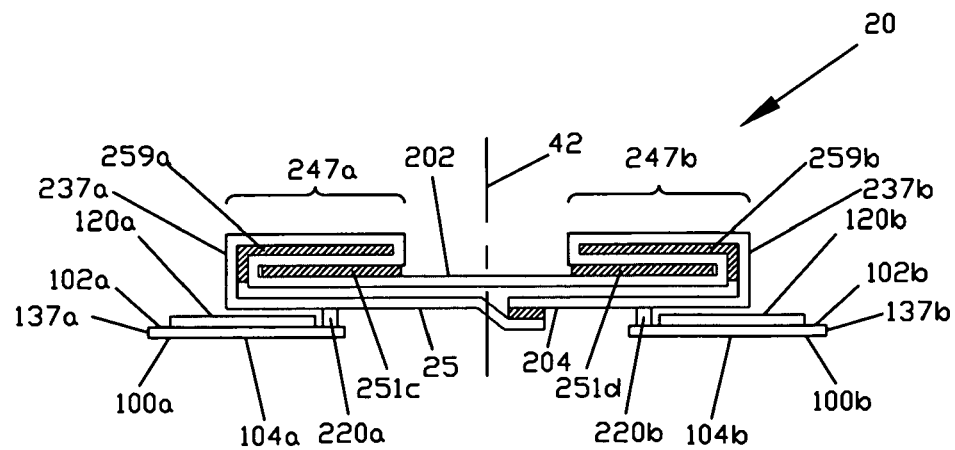
Figure 6:
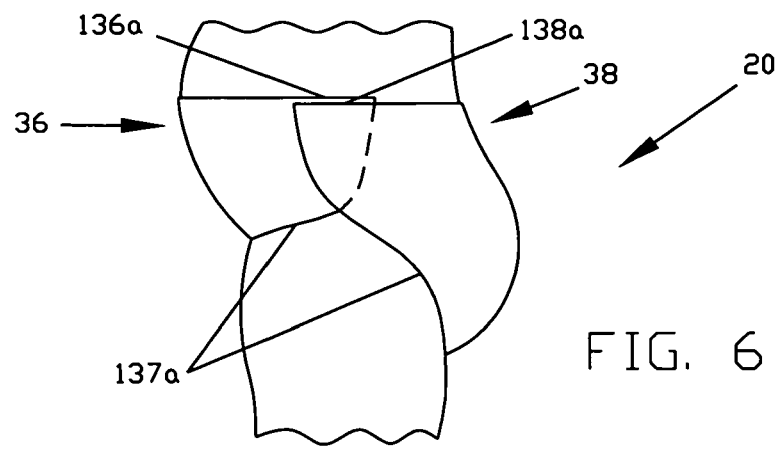
FIG. 6, FIG. 7, and FIG. 8 are respectively simplified side, front, and back elevation views of the diaper 20 of FIG. 1 being worn about the lower torso of the wearer.
Figure 7:
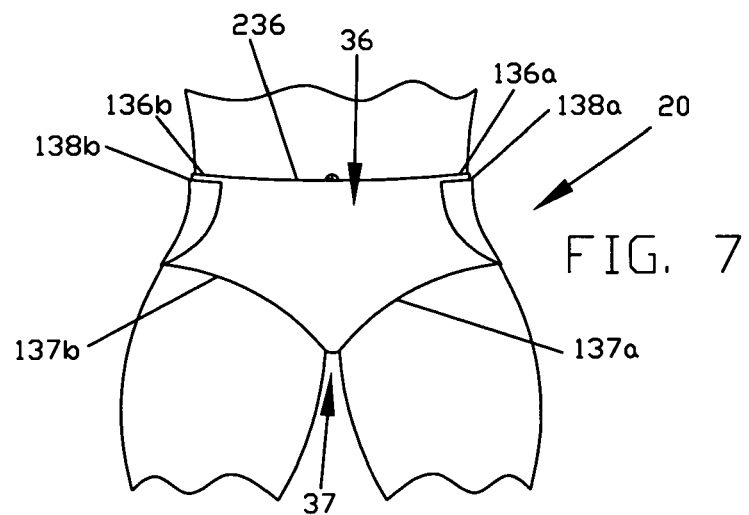
Figure 8:
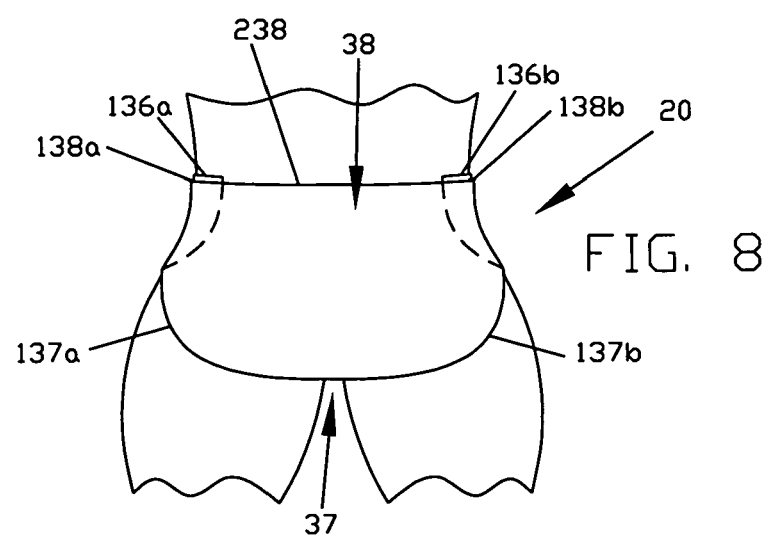

Alternatively, or in addition, the layers 27 and 28 of the doubled lower covering sheet 25 may be attached together in the waist regions 36 and 38 adjacent to the front and back edges 236 and 238 of the absorbent assembly 200, for example in laterally extending attachment zones 259 as shown in FIG. 1, FIG. 3, and FIG. 5. This lateral attachment may be laterally intermittent or laterally continuous. When such laterally extending attachment is continuous, it prevents the layers from separating and thereby presenting an undesirable unfinished appearance at the waist edges, as well as forming a barrier serving to prevent the leakage of any liquid waste from between the layers at the front and/or back edge of the absorbent assembly.

Exemplary materials suitable for use in the doubled lower covering sheet 25 include breathable polyolefinic films, microporous or other breathable formed films, breathable monolithic films, and hydrophobic nonwovens. Suitable hydrophobic nonwovens include SM (spunbond meltblown), SMS (spunbond meltblown spunbond), and SMMS (spunbond meltblown meltblown spunbond) composites. The materials of the water vapor-permeable side sheets may be selected to balance overall product economics and function. For example, a relatively inexpensive nonwoven having a relatively low basis weight may provide the requisite level of water-impermeability when it is doubled, and its relatively low cost may offset the cost associated with the use of a greater amount of material than would be used in a single-layer lower covering sheet made of a relatively more expensive nonwoven material.

The absorbent assembly and the backsheet strips may be attached together over any part or the whole of the length of the absorbent assembly. Preferably, the second layer 28 of the lower covering sheet 25 is attached to the backsheet strips in laterally opposing longitudinally extending attachment zones such as the exemplary attachment zones 220 shown in FIG. 2, FIG. 3, FIG. 4, FIG. 5, FIG. 13, and FIG. 19. The portions of the backsheet strips that lie outside such an attachment pattern are not restrained by attachment to the absorbent assembly and therefore remain extensible. For example, a relatively narrow longitudinally extending attachment zone 220 leaves the majority of the width of the respective backsheet strip 100 freely extensible and thereby allows extension of that backsheet strip 100 in the lateral direction.

Within the extent of the attachment zones, the absorbent assembly may be attached to the backsheet strips continuously or intermittently. For example, a film of an adhesive may be applied continuously over the entire area of the attachment zones and then used to continuously attach the absorbent assembly to the backsheet strips. As an alternative example, an adhesive may be applied discontinuously at and inside the boundaries of the attachment zones, such as in the form of dots, stripes, beads, spirals, etc., and then used to attach the absorbent assembly to the backsheet strips.

The absorbent core 250 may be attached to the first layer 27 of the lower covering sheet 25 over any part or the whole of the area of the absorbent core. Preferably, the absorbent core is attached on its exterior surface to the lower covering sheet in a cruciform attachment pattern, i.e., in an attachment pattern that forms or is arranged in a cross or "+" shape. The cruciform attachment pattern may be contiguous, i.e., all of its portions may be touching or connected throughout the pattern in an unbroken sequence, or may include detached portions and thereby lack contiguity but still be arranged such that the shape of the overall pattern is a cruciform. An exemplary contiguous cruciform attachment pattern 210 is shown in FIG. 15, FIG. 16, and FIG. 17. Suitable configurations of cruciform attachment patterns are disclosed in U.S. patent application Ser. No. 10/880,128 filed on 29 Jun. 2004.

When an adhesive is used for the attachment, less may be necessary in a cruciform attachment pattern than in a more extensive attachment pattern. In addition, the portions of the lower covering sheet that lie outside such a cruciform attachment pattern are not restrained by attachment to the absorbent core and therefore can be extensible. In particular, a relatively narrow longitudinally extending portion 212 of a cruciform attachment pattern 210 like that shown in FIG. 15 and FIG. 17 leaves the majority of the width of the lower covering sheet 25 in the front waist region 36 and in the back waist region 38 unrestrained by the absorbent core 250 and thereby allows extension of the lower covering sheet 25 in the lateral direction in these regions. A relatively wide laterally extending portion 214 of a cruciform attachment pattern 210 like that shown in FIG. 15 and FIG. 16 prevents the portion of the lower covering sheet 25 in the crotch region 37 to which the absorbent core 250 is attached from shifting relative to the absorbent core 250 in that region and thereby contributes to the effectiveness of the raised side flaps. For example, if the lower covering sheet in the crotch region 37 were free to shift laterally, the raised side flaps 247 might distort and fail to maintain contact with the body or become improperly positioned.

Within the extent of the cruciform attachment pattern, the absorbent core may be attached to the lower covering sheet continuously or intermittently. For example, a film of an adhesive may be applied continuously over the entire area of the cruciform attachment pattern and then used to continuously attach the absorbent core to the lower covering sheet. As an alternative example, an adhesive may be applied discontinuously at and inside the boundaries of the cruciform attachment pattern, such as in the form of dots, stripes, beads, spirals, etc., and then used to attach the absorbent core to the lower covering sheet.

The absorbent core 250 includes a storage component 272 that serves to absorb and retain liquid bodily waste materials. Suitable known materials for the absorbent core storage component include cellulose fibers in the form of comminuted wood pulp, which is commonly known as "airfelt", layers or sheets of a natural or synthetic fibrous material or materials, a superabsorbent polymer or polymers, etc. These absorbent materials may be used separately or in combination. Many known absorbent materials may be used in a discrete form, i.e., in the form of fibers, granules, particles, layers and the like. Such a discrete form of an absorbent material may be immobilized by an adhesive that attaches the discrete pieces together to form a coherent layer or that attaches the discrete pieces to a substrate layer or that attaches the discrete pieces both to each other and to the substrate layer.

The absorbent core may include an acquisition component in addition to one or more storage components. The absorbent core acquisition component serves to acquire deposited liquid bodily waste material and transfer it to the absorbent core storage component. Any porous absorbent material which will imbibe and partition liquid bodily waste material to the storage component or components may be used to form the acquisition component. Preferred materials for the acquisition component include synthetic fiber materials, open celled polymeric foam materials, fibrous nonwoven materials, cellulosic nonwoven materials, and various combination synthetic/cellulosic nonwoven materials. For example, the acquisition component may be formed of a nonwoven web or webs of synthetic fibers including polyester, polypropylene, and/or polyethylene, natural fibers including cotton and/or cellulose, blends of such fibers, or any equivalent materials or combinations of materials. Examples of such acquisition materialsare more fully described in U.S. Pat. No. 4,950,264 issued to Osborn on Aug. 21, 1990. High loft nonwoven acquisition materials suitable for the acquisition component of the present invention can be obtained from Polymer Group, Inc., (PGI), 450 N.E. Blvd, Landisville, N.J. 08326, U.S.A., under the material code designation of 98920.

Such an absorbent core acquisition component 290 is shown overlying the absorbent core storage component 272 in FIG. 15, FIG. 16, and FIG. 17. A separation sheet 292 of, e.g., a tissue or a nonwoven material, may be disposed between the absorbent core storage component 272 and the absorbent core acquisition component 290 to help ensure that none of the gel formed by a superabsorbent polymer reaches the skin of the wearer. This separation sheet 292 may extend laterally beyond the side edges 257 of the absorbent core 250 and the upper covering sheet 24 may be attached to the separation sheet 292. In this arrangement, the liquid bodily waste material that is deposited onto the upper covering sheet 24 will pass through the thickness of the upper covering sheet 24 to be absorbed by the absorbent core acquisition component 290, and some or all of it may then pass through the thickness of the separation sheet 292 and then be absorbed and retained by the absorbent core storage component 272.

Figure 18:
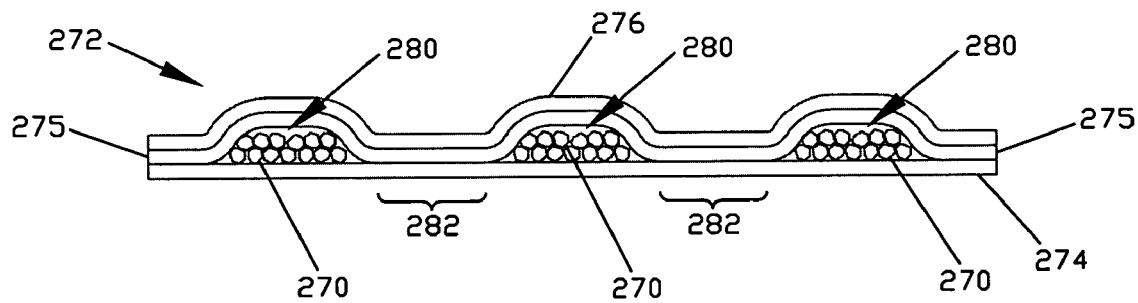
FIG. 18 is a section view of an exemplary absorbent assembly 200 showing details of an exemplary absorbent core having particles of superabsorbent material contained inside pockets

As shown in FIG. 18, in some exemplary embodiments, an absorbent core storage component 272 may include the discrete form of an absorbent material that is immobilized in pockets formed by a layer of a thermoplastic material, such as a hot melt adhesive, that intermittently contacts and adheres to a substrate sheet, while diverging away from the substrate sheet at the pockets. Absorbent core components having such structures and being suitable for the storage of liquid bodily wastes are described in co-pending and commonly assigned U.S. patent applications Ser. Nos. 10/776,839 and 10/776,851, both filed on 11 Feb. 2004. An exemplary absorbent core storage component 272 having such a structure is shown in FIG. 18. In this absorbent core storage component 272, particles 270 of a superabsorbent polymer are contained inside pockets 280 formed by a layer 275 of a thermoplastic material. The absorbent core storage component may include both particles of a superabsorbent polymer and airfelt and both materials may be contained inside the pockets formed by the layer of the thermoplastic material. Alternatively, as shown in FIG. 18, an exemplary absorbent core storage component may contain no airfelt and therefore the component can be made relatively thinner and more flexible for the comfort of the wearer. In addition, the particles of the superabsorbent polymer can be immobilized relatively more easily in the absence of airfelt. As shown in FIG. 18, the layer 275 of the thermoplastic material intermittently contacts and adheres to a substrate sheet 274 at the areas of attachment 282. Between the areas of attachment 282, the layer 275 diverges away from the substrate sheet 274 to form the pockets 280. The layer 275 may have the form of a sheet of fibers of the thermoplastic material through which the liquid bodily waste may pass to be absorbed by the particles 270 of the superabsorbent polymer.

In FIG. 18, a separate thermoplastic layer covering sheet 276 is shown overlying the layer 275 of the thermoplastic material. Alternatively, the separate thermoplastic layer covering sheet 276 may be omitted. As another alternative, two absorbent core storage components each like that shown in FIG. 18 except for the omission of the thermoplastic layer covering sheet 276 may be superposed with one absorbent core storage component inverted such that the respective substrate sheets distally oppose each other. In such a combination of absorbent core storage components, an uppermost substrate sheet may serve as an upper covering sheet.

Figure 19:
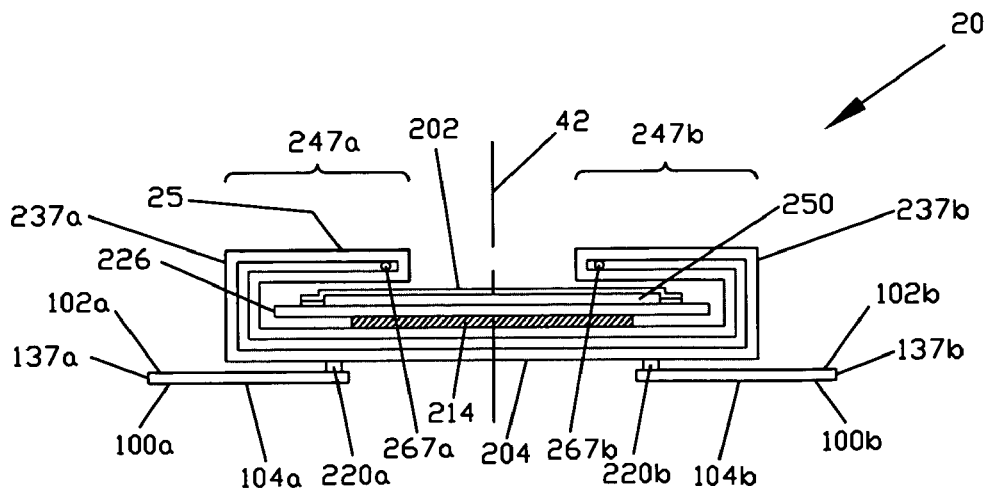
FIG. 19 is a section view of an exemplary absorbent assembly 200 having an additional bottom sheet 226, taken at a section line corresponding to the section line 4-4 in FIG. 1.

The absorbent assembly may include an additional bottom sheet to enhance the protection against leakage. Such an additional bottom sheet may be water-impermeable and may be formed of a suitable material, for example a film of polyethylene or another polyolefin, a microporous breathable film, a hydrophobic nonwoven, or a film formed of coextruded layers of polyolefin layers. For example, a suitable coextruded film is available from Clopay Plastic Products Co. of Mason, Ohio, U.S.A. under the designation of M18-327. For example, as shown in FIG. 19, an additional bottom sheet 226 may be disposed below the absorbent core 250 between the layers 27 and 28 of lower covering sheet 25. Alternatively, the additional bottom sheet may be attached to the absorbent assembly either interiorly or exteriorly of the lower covering sheet. This additional bottom sheet may extend laterally less far than either of the side edges 237 of the absorbent assembly 200, as shown in FIG. 19, or may extend laterally to overlap one or both of the side edges.

When such an additional bottom sheet is attached inside the absorbent assembly between the lower covering sheet and the absorbent core, the additional bottom sheet may be attached to the lower covering sheet in a cruciform attachment pattern similar to that shown in FIG. 15, thus leaving the portions of the lower covering sheet that lie outside the cruciform attachment pattern unrestrained by attachment to the additional bottom sheet and allowing these portions to be extensible.

Alternatively or in addition, the additional bottom sheet in such an embodiment may be attached in such a cruciform attachment pattern to the absorbent core, thus leaving the portions of the additional bottom sheet that lie outside the cruciform attachment pattern unrestrained by attachment to the absorbent core and therefore allowing these portions to be extensible. In such an embodiment, even if the additional bottom sheet is attached to the lower covering sheet in a pattern other than a cruciform, the lower covering sheet is not indirectly restrained by the absorbent core and therefore is allowed to be extensible.

Description of the Shape of the Article

The finished diaper may have a generally rectangular shape, as in the exemplary diaper 20 shown in FIG. 1 and FIG. 2. Such a generally rectangular configuration may be desirable in order to minimize the amount of waste material and the difficulty associated with the manufacture of the diaper 20. Alternatively, the diaper may have side edges 137 that are not straight, but instead are curved and/or notched, thereby giving an overall shape in plan view of an hourglass or of an "I" to the diaper 20. Such a non-rectangular configuration may be desirable in order to impart a tailored appearance to the diaper 20 when it is worn. Such a non-rectangular configuration may also be desirable in order to impart an impression that the diaper 20 will fit comfortably between the legs of a wearer.

Figure 20:
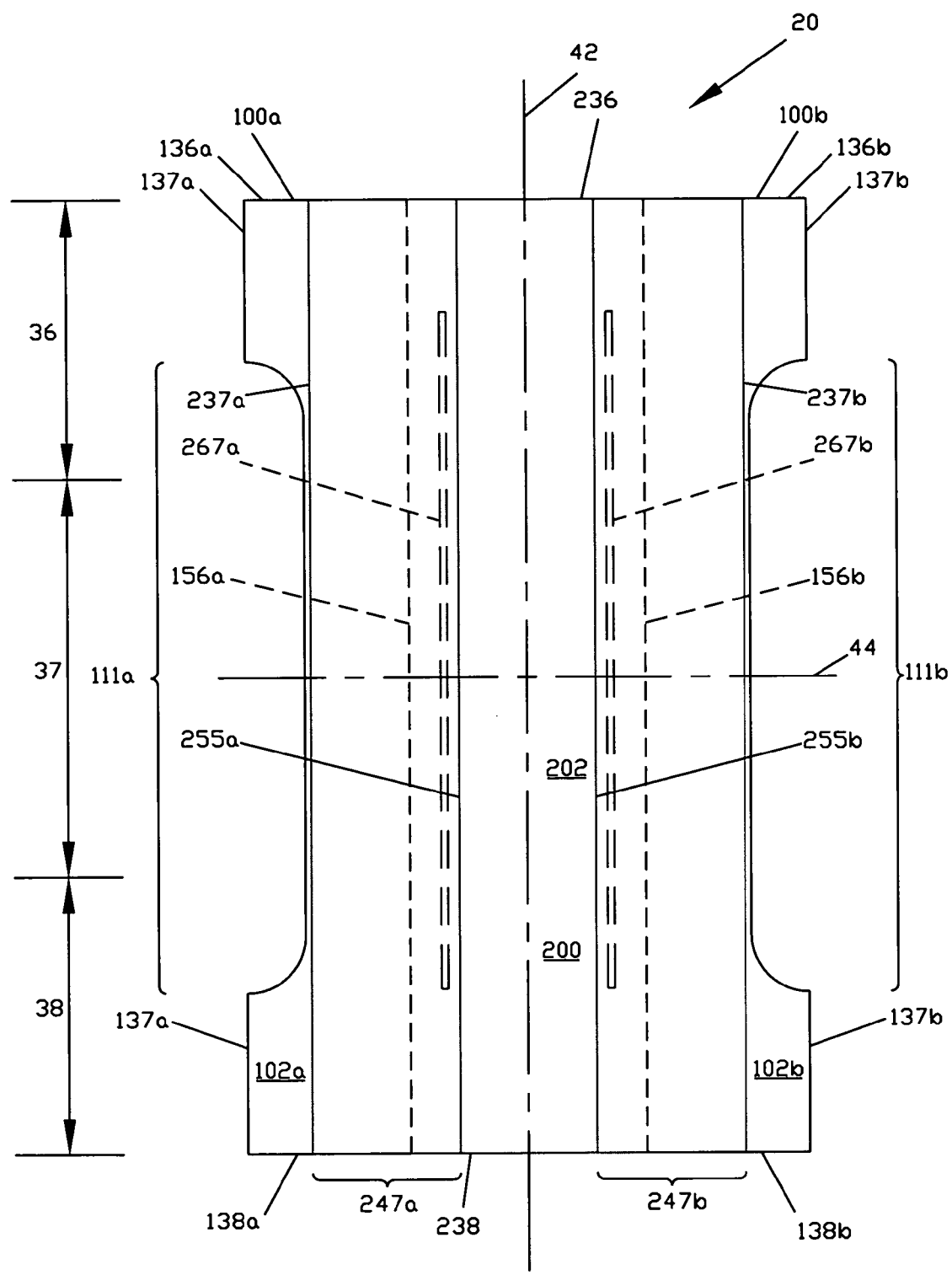
FIG. 20 is a plan view of another exemplary disposable diaper 20, which is shown in its flat, uncontracted state and with its interior portion facing the viewer.

A non-rectangular configuration of the diaper may be formed in any one of several ways. For example, laterally distal portions may be removed from the diaper to make its lateral dimension at and adjacent to the lateral axis 44 smaller than its lateral dimension at and adjacent to the front waist edge 136 and smaller than its lateral dimension at and adjacent to the back waist edge 138, i.e., to make the diaper narrower in the crotch region 37 than at the waist edges. An exemplary form of such a non-rectangular configuration of the diaper is shown in FIG. 20. As shown in this figure, portions of the backsheet strips 100 may be removed to form laterally opposing side notches 111, while leaving the backsheet strips longitudinally continuous.

Figure 21:
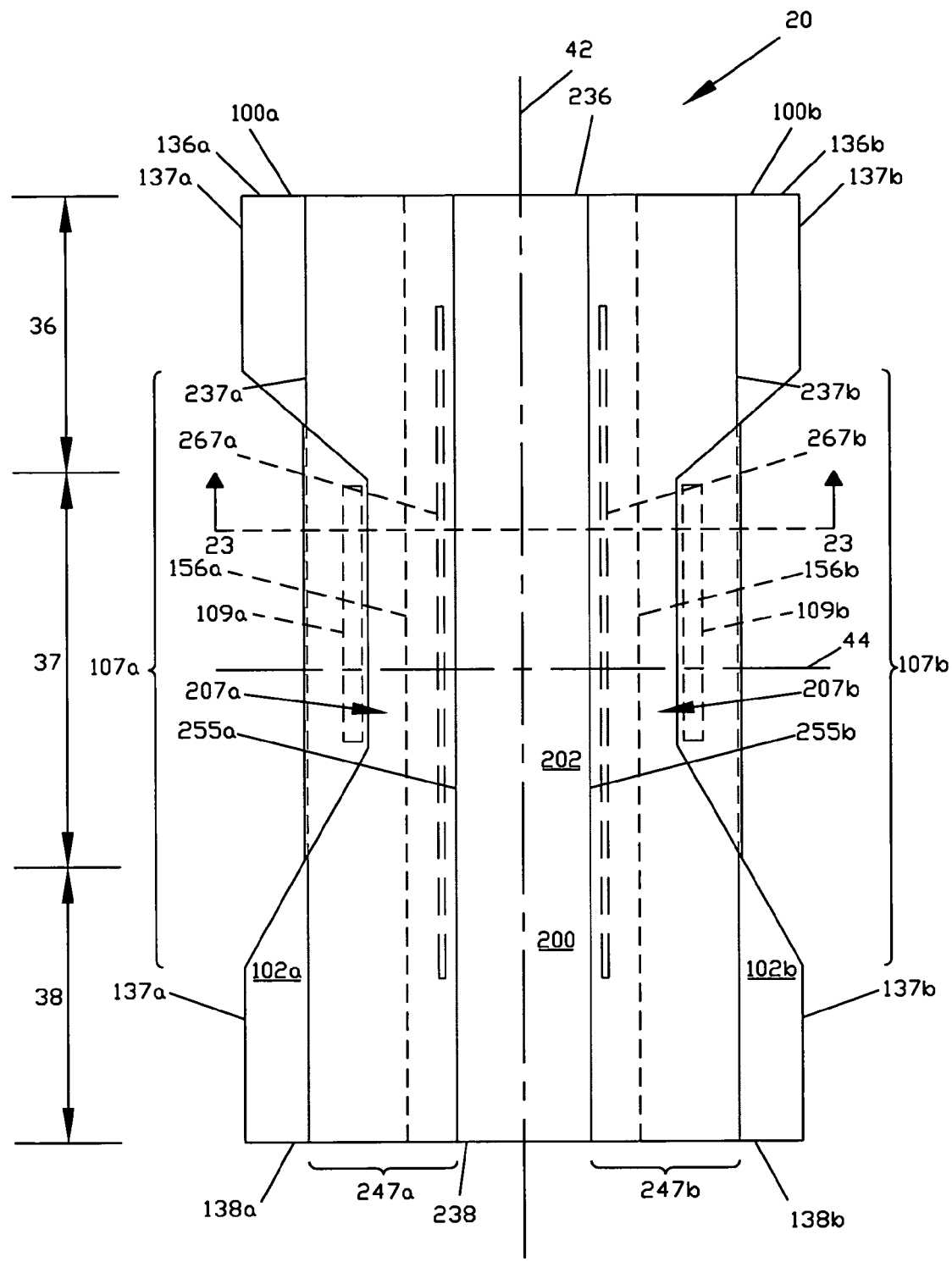
FIG. 21 is a plan view of another exemplary disposable diaper 20, which is shown in its flat, uncontracted state and with its interior portion facing the viewer.
Figure 22:
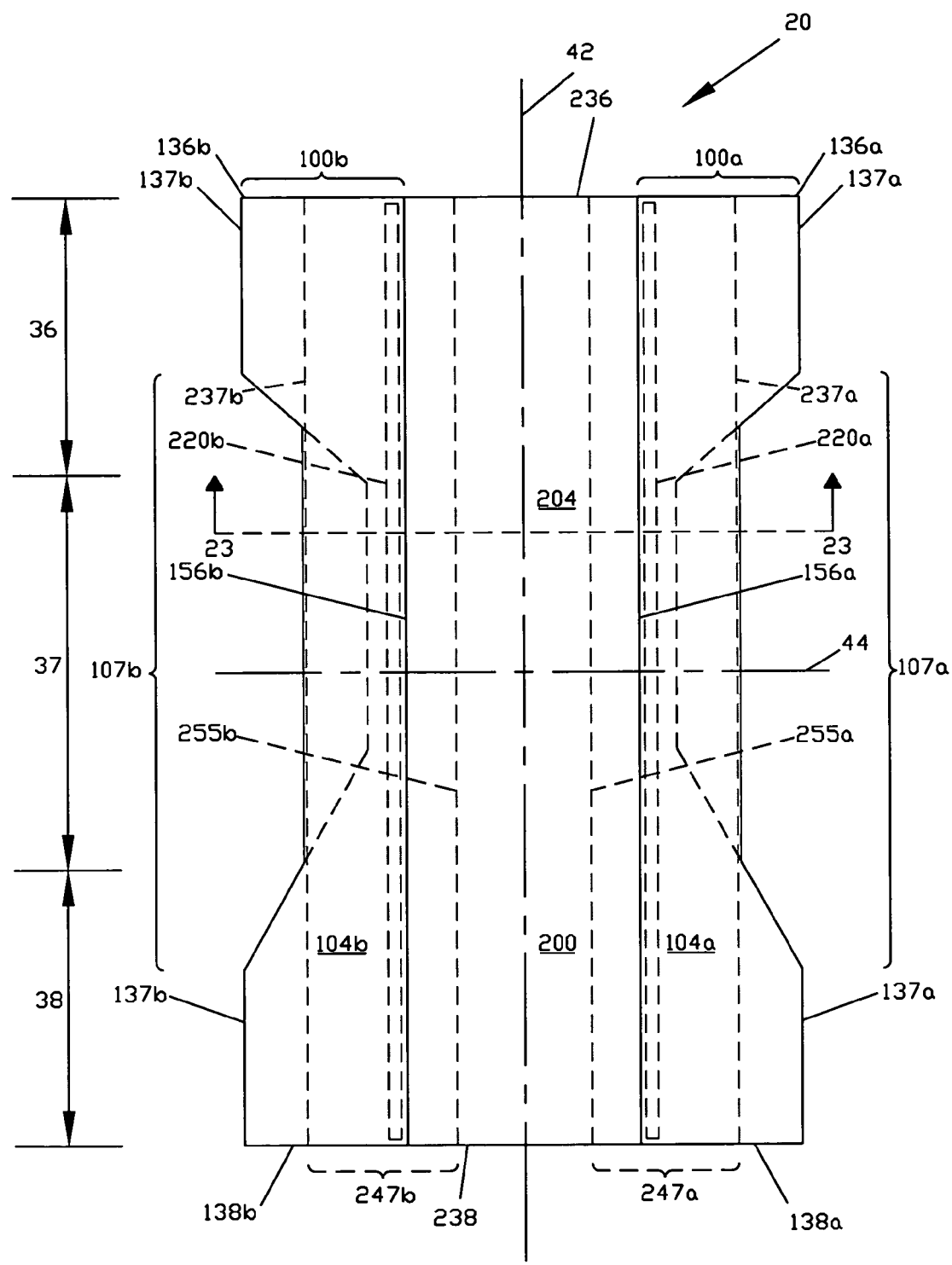
FIG. 22 is an exterior plan view of the diaper 20 of FIG. 21.
Figure 23:
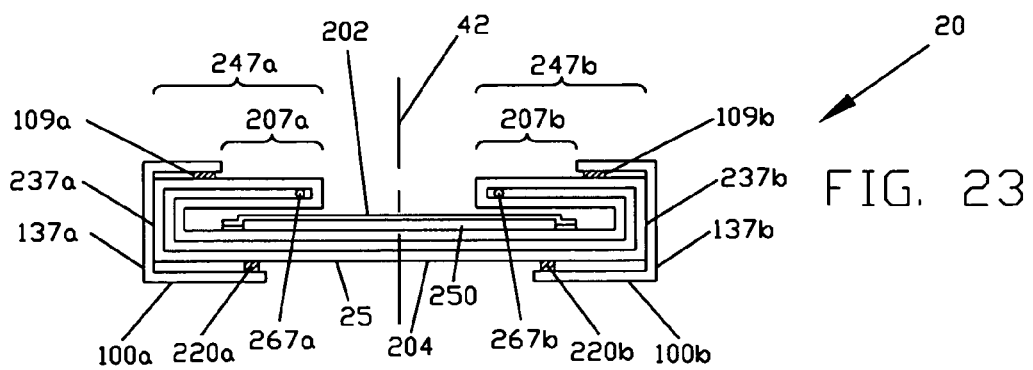
FIG. 23 is a section view of the diaper 20 of FIG. 21 and FIG. 22 taken at the section line 23-23, with its interior portion facing upward.

Alternatively, a portion of each of the backsheet strips 100 may be folded laterally inward in order to form a non-rectangular configuration of the diaper. For example, as shown in FIG. 21, FIG. 22, and FIG. 23, laterally opposing portions 107 of the backsheet strips 100 in the crotch region 37 may be folded laterally inward to overlap the respective side flaps 247 and may be attached to the side flaps, for example, in the respective attachment zones 109. Preferably, each of the folded laterally opposing portions 107 extends laterally only a part of the way from the respective side edge 237 of the absorbent assembly 200 toward the longitudinal axis 42, thus leaving uncovered respective exposed portions 207 of the side flaps, which form breathable side barriers when the diaper is worn, as described above.

Figure 24:
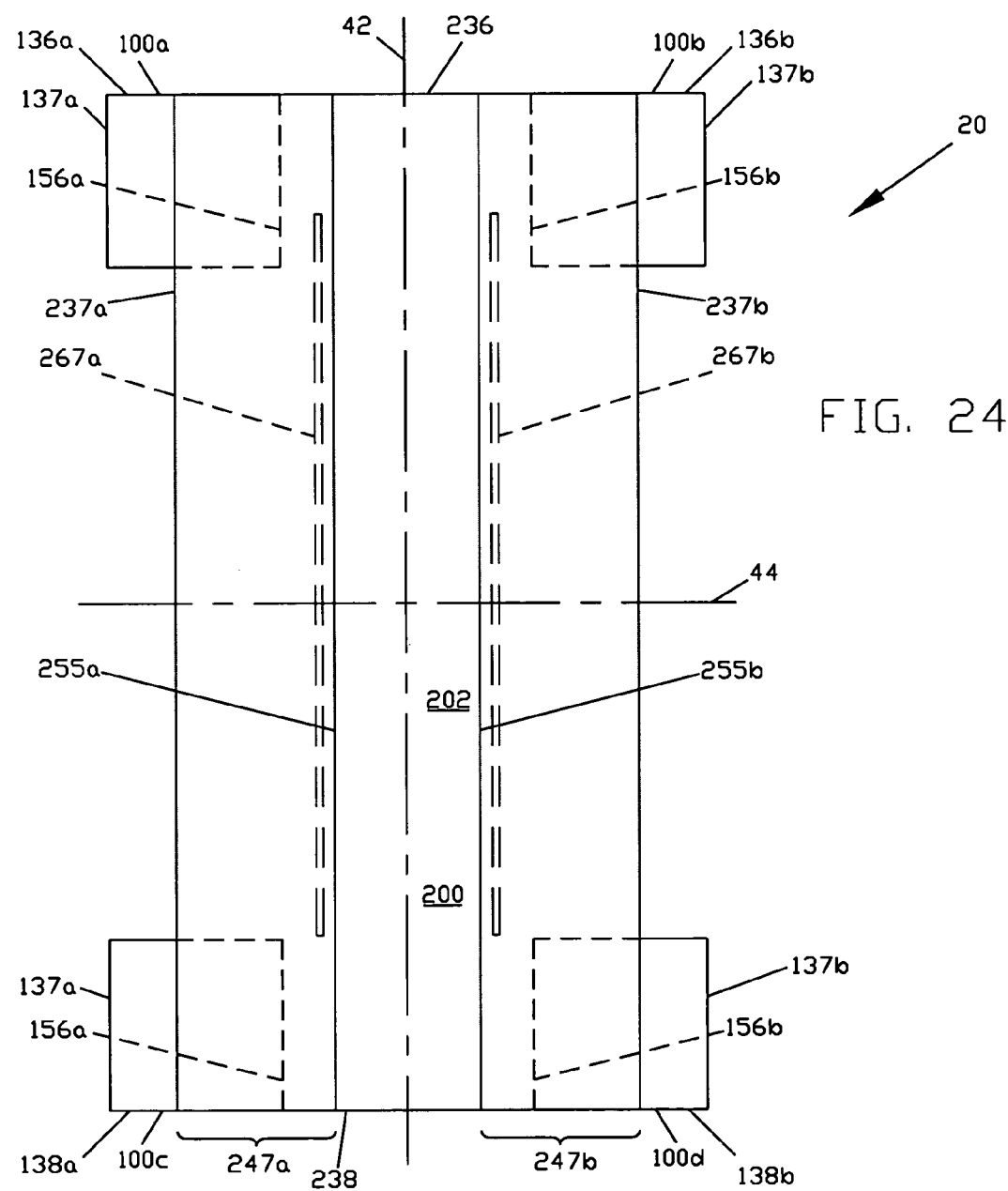
FIG. 24 is a plan view of another exemplary disposable diaper 20, which is shown in its flat, uncontracted state and with its interior portion facing the viewer.

As another alternative, the backsheet strips may be made longitudinally discontinuous in order to form a non-rectangular configuration of the diaper. For example, as shown in FIG. 24, the backsheet strips may be separated into a left front backsheet strip 100a, a left back backsheet strip 100c, a right front backsheet strip 100b, and a right back backsheet strip 100d, and each of these backsheet strips may extend laterally beyond the side edges 237 of the absorbent assembly 200, thereby imparting an "I" shape to the diaper 20.

Statements of Incorporation by Reference and Intended Scope of Claims

The disclosures of all patents, patent applications and any patents which issue thereon, as well as any corresponding published foreign patent applications, and all publications listed and/or referenced in this description, are hereby incorporated in their entireties herein by reference. It is expressly not admitted that any of the documents or any combination of the documents incorporated herein by reference teaches or discloses the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the following claims are intended to cover all such changes and modifications that are within the scope of this invention.

What is claimed is:

1. A disposable diaper having a front waist region, a back waist region, a crotch region between the waist regions, a longitudinal axis, and a lateral axis, and comprising:
    an absorbent assembly comprising an absorbent core, a lower covering sheet, a front edge, a back edge, laterally opposing side edges extending between the front edge and the back edge, an exterior surface, and an interior surface;
    wherein laterally opposing longitudinally extending portions of the lower covering sheet are folded interiorly laterally inward to form the side edges of the absorbent assembly and laterally opposing side flaps having proximal edges, the lower covering sheet being doubled by folding and thereby having first and second layers for at least a portion of the distance between each of the proximal edges and the respective side edges;
    wherein each of the side flaps are attached adjacent to its longitudinally distal ends to the interior surface and wherein each of the side flaps have a longitudinally extending elastic gathering member sandwiched between the first and second layers adjacent to its proximal edge; and
    two laterally opposing longitudinally extending backsheet strips attached to the exterior surface of the lower covering sheet.

2. The disposable diaper of claim 1 wherein the doubled lower covering sheet is water-impermeable.

3. The disposable diaper of claim 2 wherein the lower covering sheet is formed of a hydrophobic nonwoven material.

4. The disposable diaper of claim 1 wherein the absorbent assembly further comprises an additional bottom sheet disposed between the first layer and the second layer of the doubled lower covering sheet.

5. The disposable diaper of claim 4 wherein the additional bottom sheet is water-impermeable.

6. The disposable diaper of claim 5 wherein the additional bottom sheet is water vapor-permeable.

7. The disposable diaper of claim 1 wherein the elastic gathering member is sandwiched between the first layer and the second layer of the doubled lower covering sheet.

8. The disposable diaper of claim 1 wherein the proximal edges of both of the side flaps are formed by the folding of the lower covering sheet for doubling.

9. The disposable diaper of claim 1 wherein the doubled lower covering sheet has the first and second layers over substantially its entire area.

10. The disposable diaper of claim 9 wherein the lower covering sheet has two original longitudinally extending edges and the first layer and the second layer are overlapped and attached together adjacent to the original edges.

11. The disposable diaper of claim 1 wherein the first layer and the second layer are attached together in laterally spaced longitudinally extending attachment zones.

12. The disposable diaper of claim 11 wherein the laterally spaced longitudinally extending attachment zones are disposed between the proximal edges of the side flaps and the respective side edges of the absorbent assembly.

13. The disposable diaper of claim 11 wherein the laterally spaced longitudinally extending attachment zones are disposed below the absorbent core between the side edges of the absorbent assembly.

14. The disposable diaper of claim 1 wherein the first layer and the second layer are attached together in laterally extending attachment zones adjacent to the front edge and the back edge of the absorbent assembly.

15. The disposable diaper of claim 14 wherein the laterally extending attachment zones are laterally continuous.

16. The disposable diaper of claim 1 wherein when allowed the elastic gathering member is allowed to relax, the elastic gathering member contracts and lifts the proximal edge away from the interior surface of the absorbent assembly, thereby raising the side flap to form a side barrier.

17. A disposable diaper having a front waist region, a back waist region, a crotch region between the waist regions, a longitudinal axis, and a lateral axis, and comprising:
    an absorbent assembly comprising an absorbent core, a lower covering sheet, a front edge, a back edge, laterally opposing side edges extending between the front edge and the back edge, an exterior surface, and an interior surface;
    wherein the absorbent core is attached to the lower covering sheet via an attachment pattern comprising a longitudinally extending portion disposed along the longitudinal axis and at least one laterally distal portion;
    wherein laterally opposing longitudinally extending portions of the lower covering sheet are folded interiorly laterally inward to form the side edges of the absorbent assembly and laterally opposing side flaps having proximal edges, the lower covering sheet being doubled by folding and thereby having first and second layers for at least a portion of the distance between each of the proximal edges and the respective side edges, and
    two laterally opposing longitudinally extending backsheet strips attached to the exterior surface of the lower covering sheet.

18. The disposable diaper of claim 17 wherein at least a portion of the lower covering sheet lying outside the cruciform pattern is laterally extensible.

19. A disposable diaper having a front waist region, a back waist region, a crotch region between the waist regions, a longitudinal axis, and a lateral axis, and comprising:
    an absorbent assembly comprising an absorbent core, a lower covering sheet, a front edge, a back edge, laterally opposing side edges extending between the front edge and the back edge, an exterior surface, and an interior surface;
    wherein laterally opposing longitudinally extending portions of the lower covering sheet are folded interiorly laterally inward to form the side edges of the absorbent assembly and laterally opposing side flaps having proximal edges, the lower covering sheet being doubled by folding and thereby having first and second layers for at least a portion of the distance between each of the proximal edges and the respective side edges; and
    two laterally opposing longitudinally extending backsheet strips attached to the exterior surface of the lower covering sheet, each of the backsheet strips having at least one fastening element attached to it, the fastening element being adapted for fastening the front waist region and the back waist region together to encircle a waist and a leg of a wearer.

20. The disposable diaper of claim 19 wherein the fastening element includes a cohesive fastening patch.

21. A disposable diaper comprising:

a sheet comprising and an interior surface and an exterior surface and forming multiple components of the diaper, including a front waist region, a back waist region, a crotch region between the front and back waist regions, a backsheet, and barrier leg cuffs;

an absorbent assembly attached directly to the interior surface of the sheet;

wherein the sheet is folded over along first and second laterally opposing side edges, respectively, to form first and second laterally opposing side flaps, the first and second side flaps each comprising a distal folded edge running longitudinally and an opposing proximal free edge running longitudinally, wherein the interior surfaces of the sheet are directly bonded together in the font and back waist regions of the first and second laterally opposing side flaps, wherein the first and second proximal free edges of the first and second side flaps, respectively, are folded over to contain first and second longitudinally extending elastic gathering members, respectively, wherein the elastic gathering members are attached directly to the interior surface of the sheet such that the sheet gathers and forms barrier leg cuffs, and wherein a substantial portion of the sheet is extensible;

a backsheet strip attached to the exterior surface of the sheet along each of the laterally running distal folded edges of the side flaps; and one or more fasteners attached to the backsheet strips.

* * * * *

UNITED STATES PATENT AND TRADEMARK OFFICE
CERTIFICATE OF CORRECTION

PATENT NO. : 7,618,404 B2
APPLICATION NO. : 11/159916
DATED : November 17, 2009
INVENTOR(S) : LaVon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 452 days.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,618,404 B2 | Page 1 of 1 |
| APPLICATION NO. | : 11/159916 | |
| DATED | : November 17, 2009 | |
| INVENTOR(S) | : Gary Dean LaVon et al. | |

It is certified that error appears in the above-identified patent and that said Letters Patent is hereby corrected as shown below:

Title Page

Page 4, Column 1, line 50, delete "2008/0020815 A1  8/2008  LaVon, et al."

Column 3

Line 8, delete "450" and insert -- 45° --.

Column 18

Line 1, delete "font" and insert -- front --.

Signed and Sealed this

Seventh Day of December, 2010

David J. Kappos
*Director of the United States Patent and Trademark Office*